(12) United States Patent
White

(10) Patent No.: US 9,486,627 B1
(45) Date of Patent: Nov. 8, 2016

(54) FUNCTIONAL ELECTRICAL STIMULUS UNIT

(76) Inventor: Carter B. White, Mesquite, TX (US)

( * ) Notice: Subject to any disclaimer, the term of this patent is extended or adjusted under 35 U.S.C. 154(b) by 1889 days.

(21) Appl. No.: 12/589,953

(22) Filed: Oct. 30, 2009

Related U.S. Application Data

(60) Provisional application No. 61/198,294, filed on Nov. 4, 2008.

(51) Int. Cl.
*A61N 1/18* (2006.01)
*A61N 1/36* (2006.01)

(52) U.S. Cl.
CPC ............. *A61N 1/36003* (2013.01); *A61N 1/18* (2013.01)

(58) Field of Classification Search
USPC ............................... 607/1–2, 48–49, 115, 144
See application file for complete search history.

(56) References Cited

U.S. PATENT DOCUMENTS

2005/0010265 A1\* 1/2005 Baru Fassio et al. .......... 607/48

\* cited by examiner

*Primary Examiner* — Deborah Malamud
(74) *Attorney, Agent, or Firm* — Robert E. Wise

(57) ABSTRACT

A functional electrical stimulation method and device that starts electrical stimulation of a first leg of a person when a distance between a reference point on the person's first leg and the surface on which the person walks exceeds a first predetermined value and stops electrical stimulation of the first leg of the person when the distance between the reference point and the surface falls below a second predetermined value, wherein the first and second predetermined values are calculated from an initial measurement of the distance between the reference point and the surface when the person is standing still and the first leg is perpendicular to the surface. The first predetermined value is greater than the second predetermined value. The method and device produce a more natural gait in persons with drop foot, and minimize the time electrical stimulation is applied to muscles so as to minimize muscle fatigue.

21 Claims, 18 Drawing Sheets

Outside view of the leg and foot

Outside view of the leg and foot

The Setup Remote

FUNCTIONAL ELECTRICAL STIMULUS UNIT

REFERENCE TO RELATED APPLICATION

This application claims the benefit of 35 U.S.C. §111(b) Provisional Patent Application Ser. No. 61/198,294 which was filed on Nov. 4, 2008 and entitled "Functional electrical stimulus unit".

FIELD OF THE INVENTION

The present invention relates to an apparatus worn by a person that has a condition known as "drop foot". The present invention is a portable functional electrical stimulus (FES) apparatus that is intended to be worn by persons who by disease or injury or defect are unable to lift the foot while walking. The present invention electrically stimulates the nerve to cause the tibialis anterior muscle to lift the foot during the appropriate time of the swing phase of walking.

BACKGROUND OF THE INVENTION

Drop foot occurs when the nerve stimulation from the central nervous system has slowed or lost connection to the tibialis anterior muscle that lifts the foot during walking. This condition occurs for several reasons, some of which are caused by an accident involving the spinal cord, a stroke, neuropathy, a nervous system disease or any nervous system disconnect that causes the loss of nerve to muscle communication. The devastating effects of this condition result in the inability to walk. The drop foot disability can create emotional and financial hardships for the affected person and their family.

There have been many attempts to help a person with the drop foot condition. The most commonly used device is a brace that limits the foot dropping below a predetermined point. Springs and motors also, have been used to lift the foot. Within the past twenty years, researchers have been electrically stimulating the nerve to flex the muscle that lifts the foot. Physical therapists use electrical stimulation to exercise and rehabilitate injured or paralyzed muscles. Electrodes are placed on the skin over the nerve and muscle and a stimulator device sends electrical pulses to the electrodes that stimulate the muscle.

Portable functional electrical stimulus patents date back to 1954 with U.S. Pat. No. 2,737,183 to Graimo. The patient pressed a switch to start and stop the electrical stimulation. In 1963, U.S. Pat. No. 3,083,712 to Keegan taught a device that initiated electrical stimulation by a heel switch placed under the foot. The use of a foot switch requires the patient to wear shoes. While standing or sitting weight must be shifted to the foot, with the foot switch, to prevent false stimulation. The point the stimulation ends is when the foot switch is activated after the foot contacts the walking surface. Tilt switch and foot switch combinations are described in U.S. Pat. No. 4,796,631 to Grigoryer. A biofeedback-activated electromechanical device is described in U.S. Pat. No. 5,112,296 in 1992. Activation of an electric motor to lift the foot was initiated from muscle activity sensing through skin surface electrodes. U.S. Pat. No. 5,643,332 to Stein in 1997 describes a tilt switch mounted in a device placed under the knee. The tilt switch activates the stimulator at a predetermined angle of the leg. Tri-axis motion sensors are used in U.S. Pat. No. 7,369,896 to Gesotti in 2008 to stimulate muscles to improve motion disorders. Stimulation timing is critical for an FES apparatus to be usable. The prior art addresses this timing issue by either using a foot switch, a tilt switch, motion sensors, or any combination of these sensors to initiate the stimulation.

Other prior art that uses a tilt switch to begin and end stimulation, must be set to a predetermined point when the angle of the leg is at the correct position for stimulation. Since the angle for beginning stimulus is preset, the placement of the controller on the leg is critical for proper function and stimulation. Walking on level ground is also another limiting factor. An inclined surface changes the tilt angle and can cause improper stimulation. In some devices, after the stimulation begins the timing is set to end the stimulation, requiring the patient to walk at that preset pace and stride. Any change in motion and stepping cycle causes false stimulation. Prior art that uses a foot switch to control stimulation must be hard wired or use a wireless transmitter that sends a signal to a control unit in order to determine when to start and stop the nerve stimulation. Prior art is complicated to set up, difficult to operate and wear, and expensive for the patient. These devices require extensive training for the clinician and the patient.

OBJECT OF THE PRESENT INVENTION

The object of the present invention is to provide a small portable Functional Electrical Stimulator (FES) that is easy to wear, simple to use, and inexpensive to manufacture. The key to better functioning is the ability to stimulate the muscle, raise the foot, and then lower the foot as if there is no disability. The gait of a person, who does not have a walking disability, is constantly changing to compensate for changing conditions of the walking surface. The time the foot stays lifted in the swing phase may be more or less depending on decisions made, avoiding obstacles, stepping up stairs, or walking down an incline. The present invention uses a distance sensor and microcontroller to imitate a natural walking cycle.

The present invention begins and ends the electrical stimulation by measuring the distance from a fixed device worn on the affected leg to the walking surface. The present invention is able to track the location of the foot at any time before lifting, as the foot is lifted, while the foot is in the swing phase, and at the point, the stimulation should end. If the gait changes, the present invention reacts to the change causing a natural walking cycle. The present invention can be worn anywhere below the knee and above the ankle, on the outside portion of the leg. Persons of ordinary skill in this art can adapt the present invention to be worn on any other part of the human body.

At the time the present invention is switched on, distance calculations are performed and setup parameters are entered, automatically adjusting to the position where the present invention is worn on the leg. The present invention operates with or without shoes. There is no need for weight on the leg to prevent stimulation. The present invention begins to ramp-down stimulation before the foot meets the walking surface, resulting in a natural end to the walking cycle.

The present invention is a battery-powered portable device that is contained in one small enclosure, called the control unit. The control unit is held in place on the leg by a hook and loop strap. The control unit can be made very lightweight. Connected to the control unit are electrodes that provide electrical stimulation to the user. The electrodes are adhered to the skin over the nerve and muscle causing the disability. A small wireless remote control unit, called the pocket remote, can be used by the patient to turn the control unit on and off, or to switch the control unit to standby when the user stops walking for a time. Another wireless remote control device, called the setup remote, is provided for a clinician or other person to test and configure the parameters of the control unit to meet the individual requirements of the patient. The clinician can test the output pulse width and frequency, set the ramp-up and ramp-down time periods for stimulation, and set other values that are transmitted to the control unit. These settings are permanently stored in non-volatile memory in the microcontroller of the control unit, but can be changed as needed with the setup remote. The patient identification number and associated data can be stored in non-volatile memory of the microcontroller in the setup remote unit.

DETAILED DESCRIPTION OF THE PREFERRED EMBODIMENT

Figure 1:
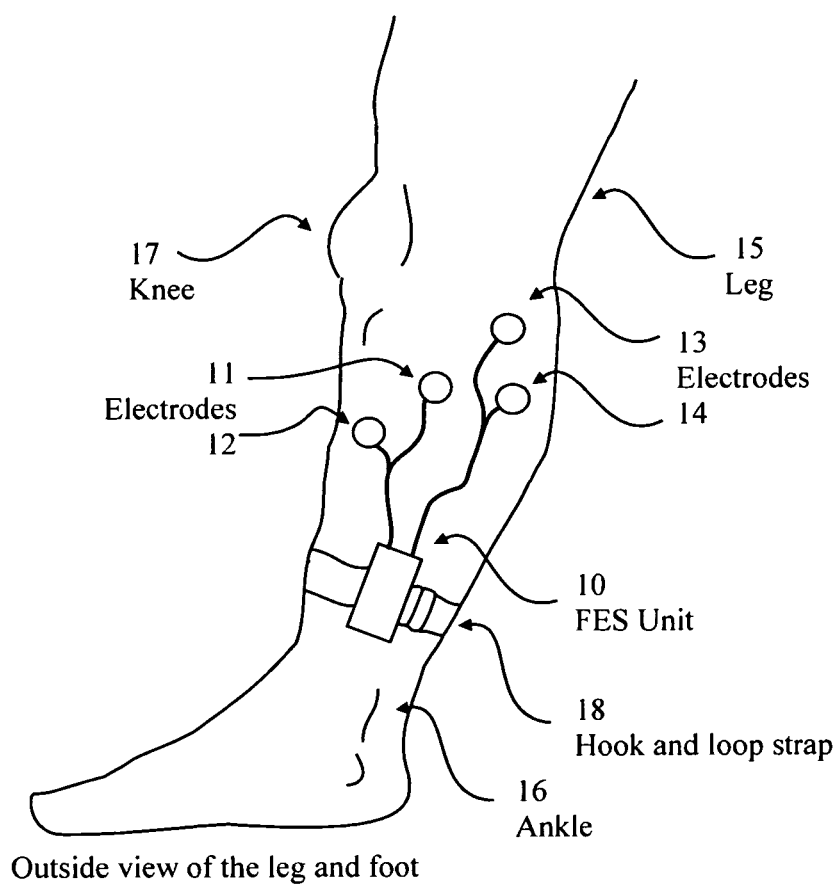
FIG. 1 shows a preferred embodiment of the control unit strapped to the patient's leg.

FIG. 1 shows a user wearing a preferred embodiment of the control unit of this invention on the user's leg. The control unit 10 is securely held, preferably on the outside of the user's leg 15, by a strap 18 that can be opened and closed with a hook-and-loop closure. The control unit 10 is preferably worn below the knee 17 of the user and above the ankle 16. Usually, it will be better to wear the unit just above the ankle. The reason for choosing this location is that, if the user wears long pants, the pant leg will tend to interfere with the distance sensor of the control unit 10. If the user's clothing were such that it would not interfere with the distance sensor, then the control unit could be worn on almost any place on the user's body where it could consistently be able to measure the distance from the control unit to the ground. The control unit is preferably removably attached to the body of the user under the user's clothing. Although the unit could be attached over one or more pieces of clothing, the clothing will tend to move along the person's body or leg to an extent that will adversely affect the function of the FES unit. The control unit 10 could be worn on the inner part of the leg 15, but the control unit may be large enough that the user might bump or hit it with his or her other leg, and adversely affect the function of the FES unit or hurt the user's leg. Connected to the control unit 10 are plural output leads that connect to electrodes that are removably attached to the user's leg. Positioning the electrodes for stimulating the muscles that will lift the foot is known in this art.

Figure 2:
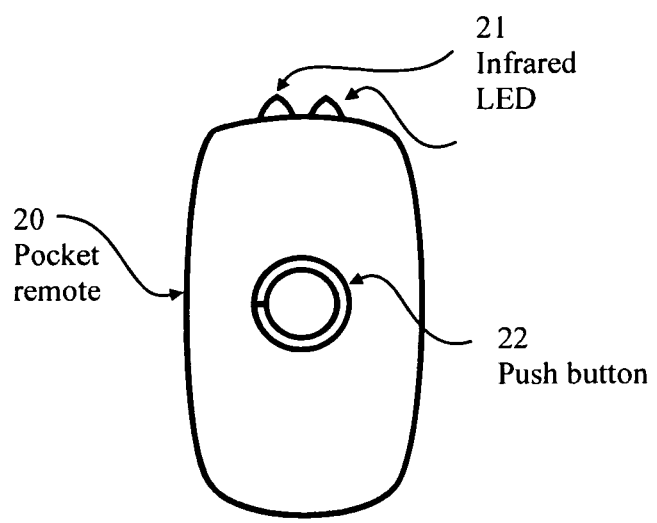
FIG. 2 shows a preferred embodiment of the pocket remote.

FIG. 2 shows a preferred embodiment of the pocket remote 20. It is a small electronic device that functions as a remote control to place the control unit 10 in a powered-down state when not in use or to power up when ready for use. This function is accomplished by pointing the pocket remote 20 at the control unit 10 and pressing the push button 22. Two infrared-emitting diodes 21 function as outputs to transmit asynchronous serial data to the control unit 10. Typically, the user would carry the pocket remote 20 whenever the FES is worn by the user. The user could typically carry the pocket remote 20 in a pocket or a purse or in the user's hand.

Figure 3:
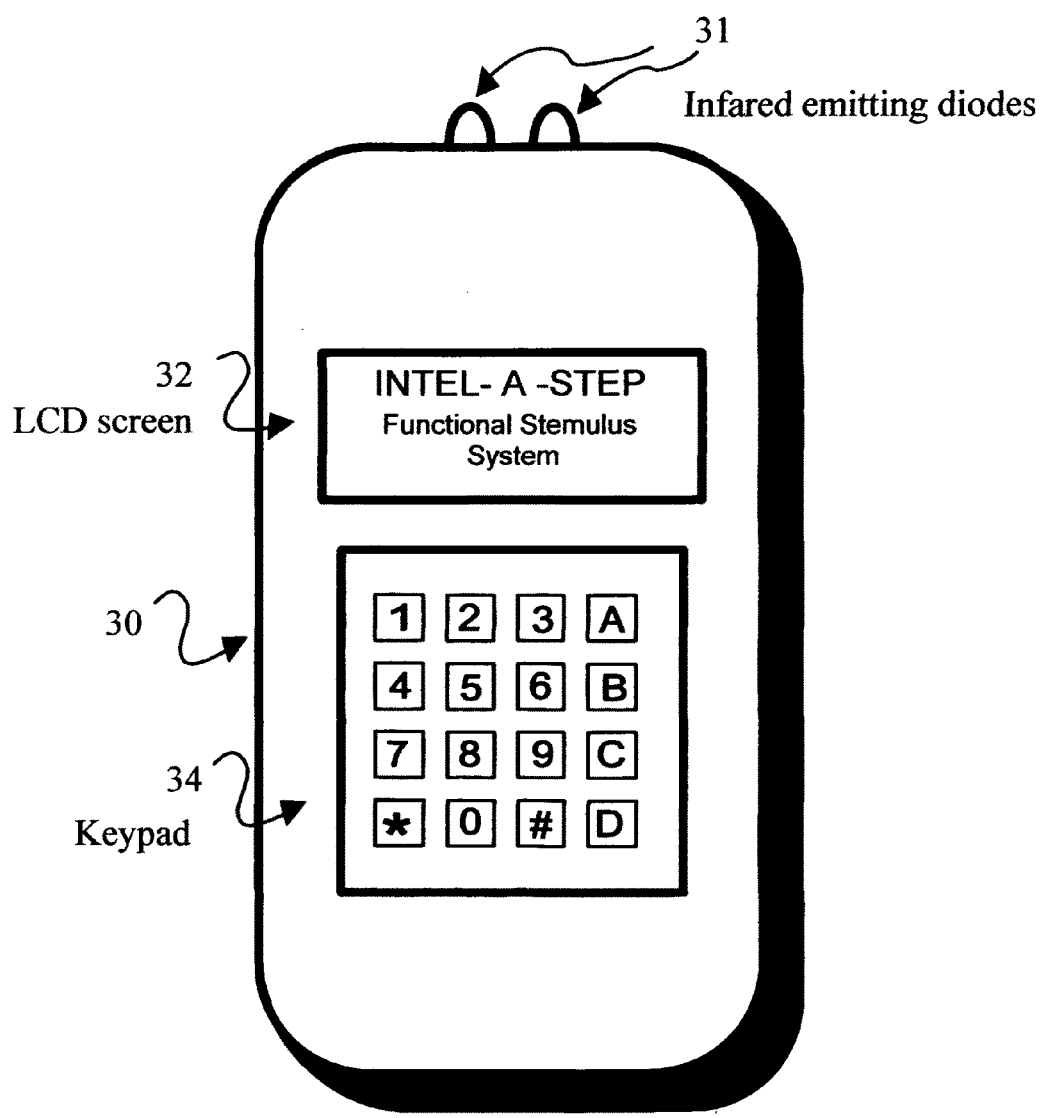
FIG. 3 shows a preferred embodiment of the setup remote.

FIG. 3 shows a preferred embodiment of the setup remote 30. It is an electronic device that functions as a remote control to test or change operating values for the control unit 10. Two infrared emitting diodes 31 function as outputs to transmit asynchronous serial data to the control unit 10. Liquid crystal display 32 provides visual information of values and command options, such as pulse width, frequency, and other operating values used to transmit to the control unit 10. Keypad 34 is a four by four-matrix keyboard with sixteen keys. Keypad 34 is used as an input device on the setup remote 30. Values are typed on the keypad 34 and displayed on the LCD screen 32. The letters on keypad 34 function as menu choices to save, cancel, or exit a function or mode. The setup remote 30 is typically kept either in a clinician's office or in the user's home, or both, or in another place. The user would typically not carry the setup remote 30 with him or her during normal usage of the FES unit. Although the particular arrangement of the setup unit 30 shown in FIG. 3 is preferred, persons of ordinary skill in this art are capable of providing different arrangements that accomplish the same general function.

Figure 4:
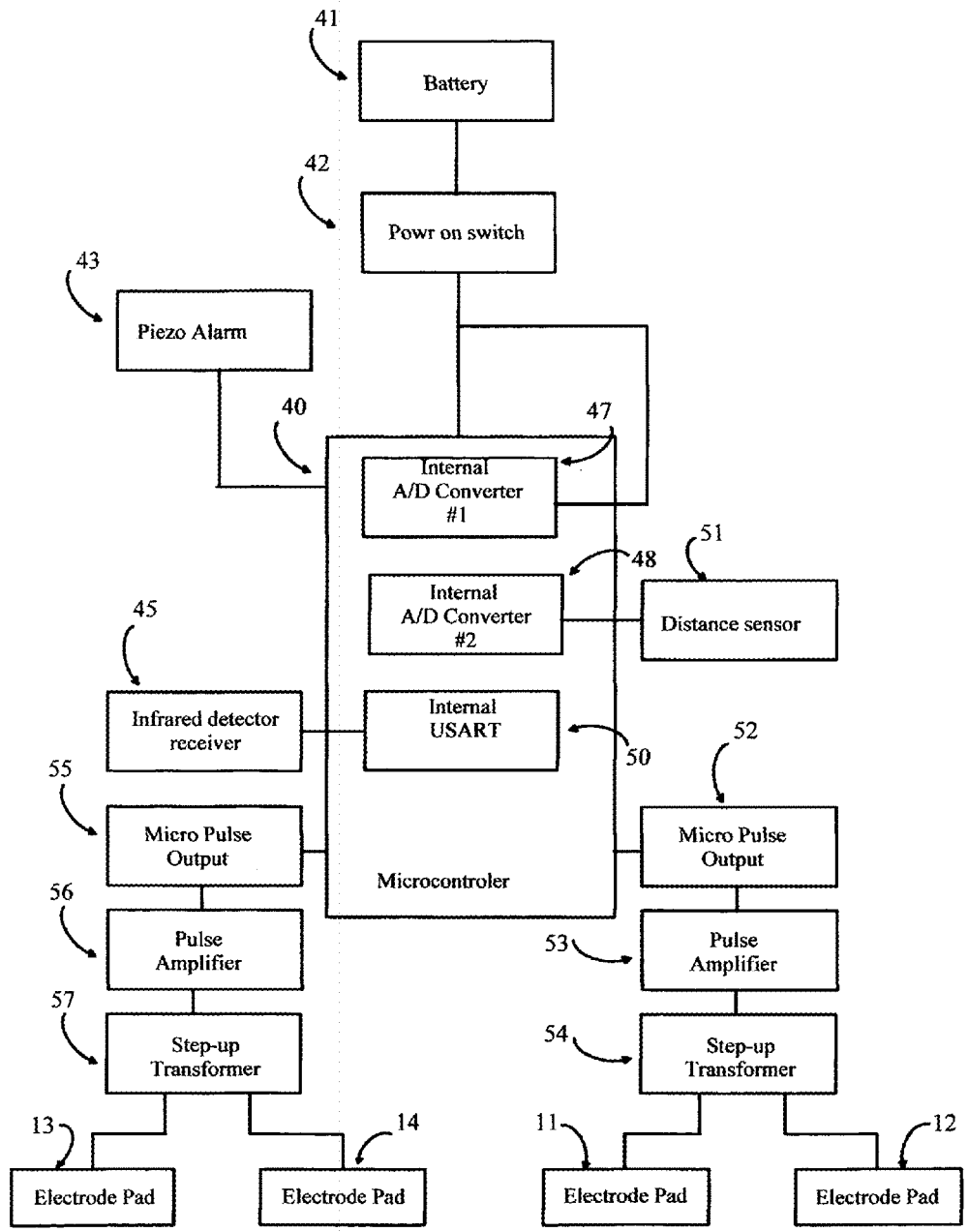
FIG. 4 is a block diagram that describes a preferred embodiment of the control unit.

FIG. 4 shows a block diagram of the preferred embodiment of the control unit 10. The battery 41, typically a rechargeable or alkaline 9-volt battery, supplies the power and is connected through the power switch 42 to the control unit microcontroller 40. When switched on, microcontroller 40 loads the pre-program instructions stored in internal non-volatile flash memory which is described in detail later herein. The microcontroller's internal peripheral modules include analog-to-digital converters numbered 47 and 48, and a Universal Synchronous Asynchronous Receiver Transmitter (USART) 50. The internal analog-to-digital converter 47 converts the battery 41 analog voltage to a digital value utilized in the program of microcontroller 40. A piezoelectric speaker 43 generates an alarm when the battery 41 voltage gets below a predetermined value, and generates alerts when values and commands are received from the setup remote 30. The internal analog-to-digital converter 48, converts the analog signal from the distance sensor 51 to a digital number that is utilized in the program of the microcontroller 40 to begin and end the channel 1 micro-pulse output 52 and channel 2 micro-pulse output 55. The channel 1 micro-pulse output 52 is amplified by the amplifier 53. The amplified pulse voltage of channel 1 is isolated and increased by the step-up transformer 54. The output of step-up transformer 54 is connected to electrode pads 11 and 12 that can be removably attached to the surface of the skin of the user as shown in FIG. 1. The channel 2 micro pulse output 55 is amplified by the amplifier 56. The amplified pulse voltage of channel 2 is isolated and increased by the step-up transformer 57. The output of step-up transformer 57 is connected to electrode pads 13 and 14 that can be removably attached to the surface of the skin of the user as shown in FIG. 1.

The internal USART 50 is configured in the software program of microcontroller 40 as an asynchronous serial communication receiver. The preferred embodiment of this invention utilizes an infrared receiver detector 45 to detect and demodulate the signal to an asynchronous serial communication signal. The USART detector receiver 45 may also be other types of detectors such as a detector that detects reflected radiation in bands other than the infrared, or radio frequency detector, or an ultrasonic sound detector. The modulated asynchronous serial signal originates from the pocket remote 20, as described later herein, and causes microcontroller 40 to change the power consumption of the control unit 10. When the control unit 10 is operational, the power consumption is approximately 40 milliamps. When the pocket remote 20 transmits a modulated asynchronous serial digital signal, the infrared detector receiver 45 demodulates the asynchronous serial signal. The USART 50 decodes the serial signal to a digital value. The software program reads the value and causes the microcontroller 40 to power down the control unit, thus reducing battery power consumption to approximately 95 percent.

The USART 50 also receives data transmitted from the setup remote 30. The setup remote 30 transmits a modulated asynchronous serial digital signal that the USART 50 receives and decodes the serial signal to data. The data is used by the software in the microcontroller 40 to set pulse widths, frequency values, and ramp-up and ramp-down time periods. The setup remote can also be used to transmit to the control unit any other desired input that the control unit is capable of receiving.

Figure 5:
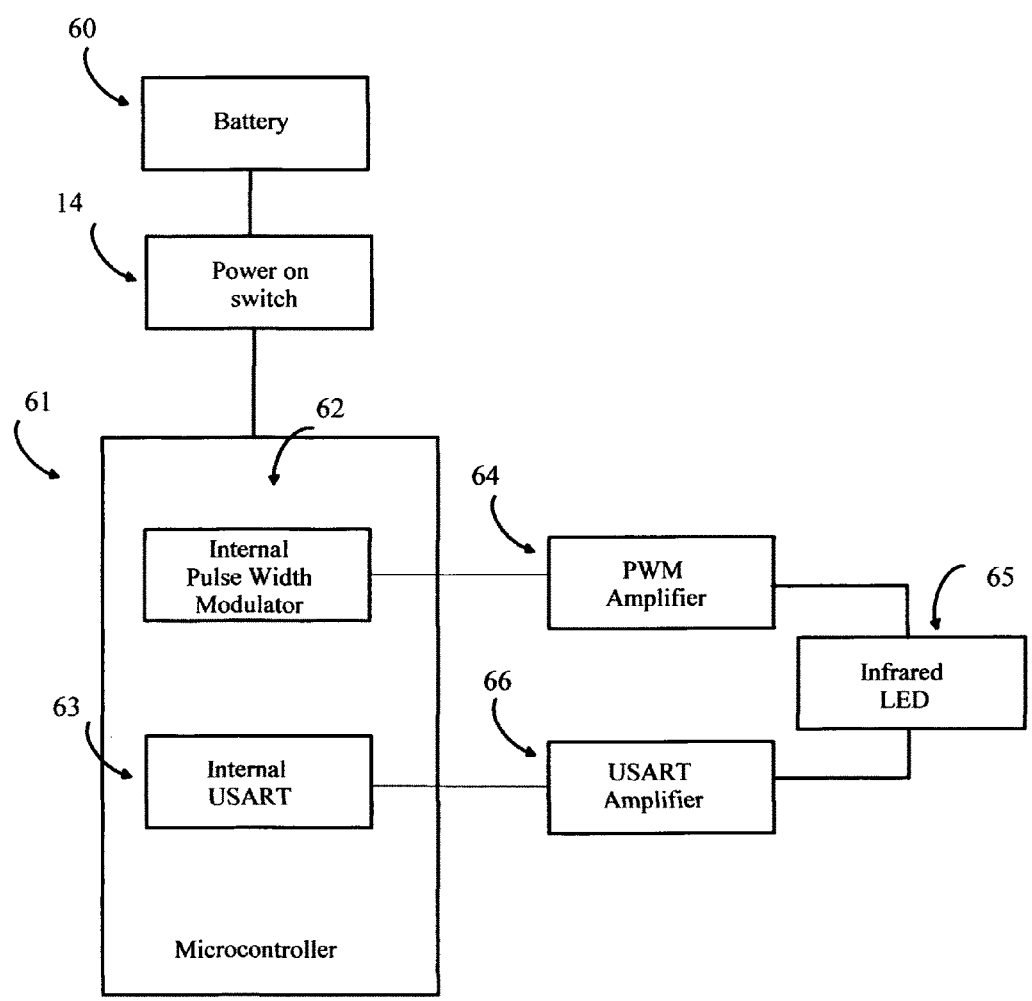
FIG. 5 is a block diagram that describes a preferred embodiment of the pocket remote.

FIG. 5 shows a block diagram of a preferred embodiment of the pocket remote 20 that functions as a power-down and power-on remote control for the control unit 10. The battery 60 can be a combination of three alkaline battery button cells to output a value of approximately 4.5 volts. The push button switch 22 puts power to the pocket remote microcontroller 61. The microcontroller 61 software program, that is stored in internal non-volatile flash memory, initializes the internal peripheral pulse width modulator 62 (PWM) and internal peripheral USART 63. The program sets the PWM 62 output frequency to approximately 38 kilohertz. The USART 63 is programmed to output an asynchronous serial signal with a preset digital signal to the USART amplifier 66. The PWM amplifier 64 and the USART amplifier 66 mix the two signals to produce a modulated asynchronous digital signal output to the infrared emitting diodes (LEDs) 65. The digital signal output can also be sent by other means such as light outside the infrared spectrum, radio-frequency radiation, or ultra-sonic sound that matches to the type of USART receiver/detector 45 of FIG. 4.

Figure 6:
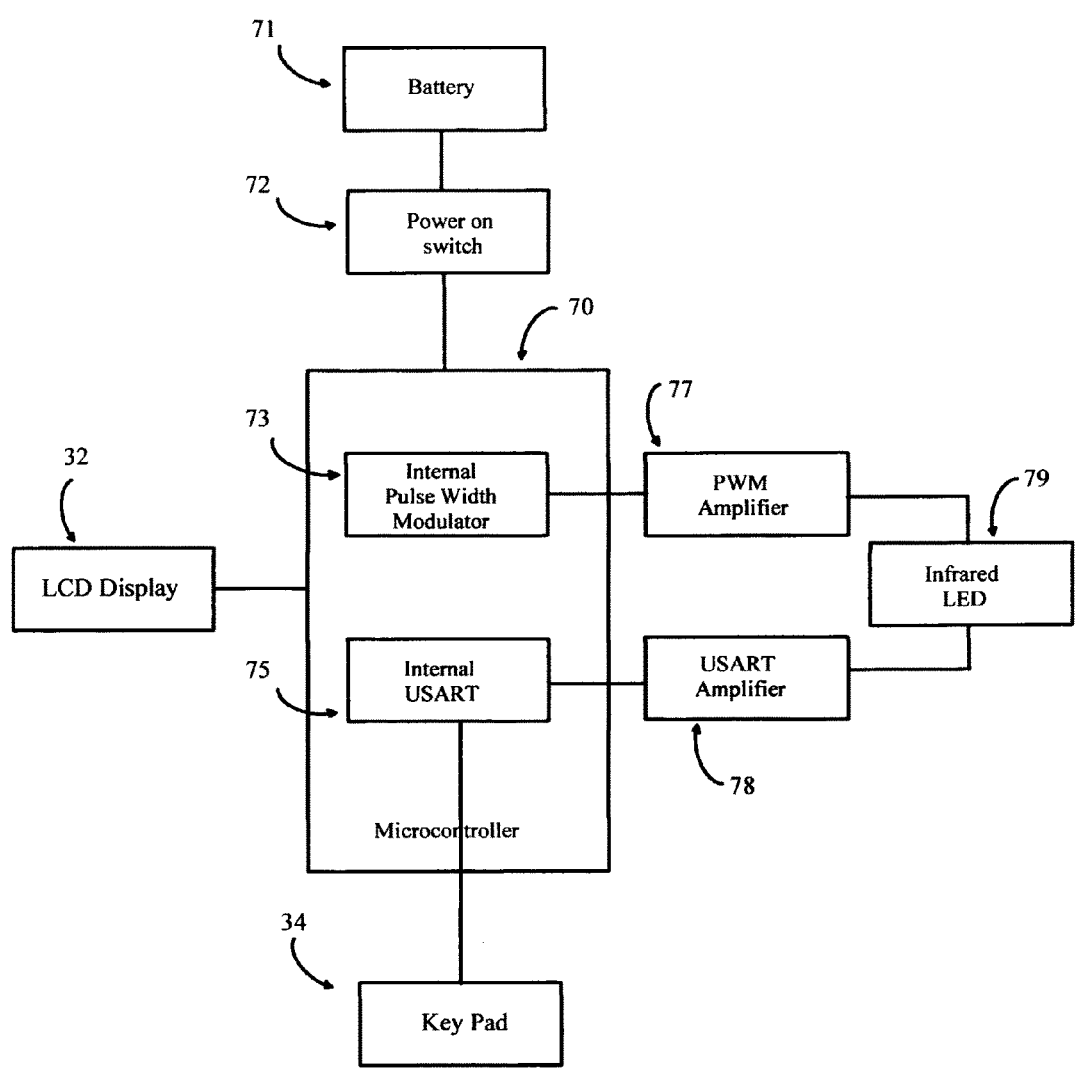
FIG. 6 is a block diagram that describes a preferred embodiment of the setup remote.

FIG. 6 illustrates a block diagram of the setup remote 30. The battery 71, a rechargeable or alkaline 9-volt battery, supplies the power for the setup remote 30 and is connected through the power switch 72 to setup remote microcontroller 70. When switched on, microcontroller 70 loads the pre-program instructions stored in its internal non-volatile flash memory which is described in detail later herein. A sixteen-key four-by-four matrix keypad 34 is an external peripheral user interface that allows the clinician to place the control unit 10 in receiver mode and input values and commands from the setup remote 30. The liquid crystal display (LCD) 32 is a peripheral used to visually display the menus with options to enter values commands that respond to keys pressed on keypad 34. The microcontroller 70 internal peripheral modules include a pulse width modulator 73 (PWM), and a Universal Synchronous Asynchronous Receiver Transmitter (USART) 75. The program sets the PWM 73 output frequency to approximately 38 kilohertz. The USART 75 is programmed as a transmitter to output an asynchronous serial signal. The setup remote 30 functions as a remote control that enables a clinician, or other person, to adjust the values that set the pulse width, frequency, and ramp-up and ramp-down variables of the stimulus given to the user, to meet the individual requirements of the patient. The setup remote 30 transmits values and control commands to the control unit 10. The functions are described in detail later herein. The USART 73 sends the data in serial form to the USART amplifier 78. The 38 kilohertz signal from the PWM 73 is sent to the PWM amplifier 77. The PWM amplifier 77 and the USART amplifier 78 mix the two signals to produce a modulated asynchronous digital signal output to the infrared light emitting diodes (LEDs) 79. The digital signal output can also be sent by other means such as light outside the infrared spectrum, radio-frequency radiation, or ultra-sonic sound that matches to the same type of USART receiver/detector 45 of FIG. 4.

Figure 7:
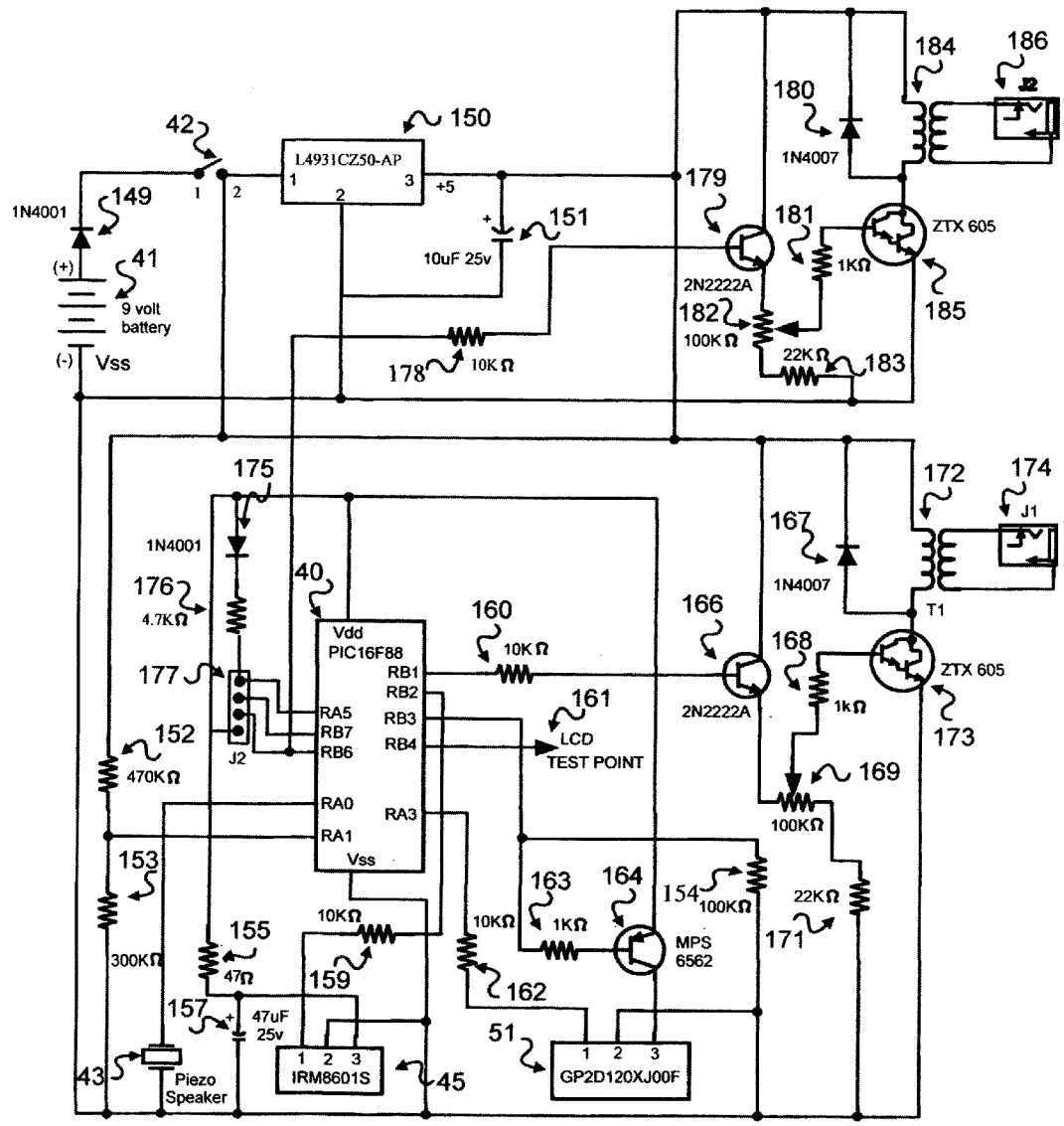
FIG. 7 is an electrical schematic diagram of a preferred embodiment of the control unit.

FIG. 7 is an electrical schematic diagram of the preferred embodiment of the control unit 10. This particular circuit diagram functions well as the control unit, but persons of ordinary skill in this art can design different circuits that accomplish the same general function. Power for the control unit 10 can be supplied by a common 9-volt alkaline or nickel metal hydride rechargeable battery 41. The positive terminal of battery 41 connects to the anode of the diode 149. The diode 149 protects the electronic components in the control unit 10 from accidental reverse polarity while installing the battery. The negative terminal of the battery 41 is connected to the Vss bus of the circuit of FIG. 7. The cathode of the diode 149 is connected to terminal 1 of the power switch 42 Terminal 2 of power switch 42 is connected to the input of the 5-volt liner voltage regulator 150 and to the +9 volt bus of the circuit of FIG. 7. The Vss terminal of the voltage regulator 150 is connected to the Vss bus in the circuit of control unit 10.

The voltage regulator 150 supplies a regulated+5 volts to the Vdd bus in the circuit of the FES Unit 10. Capacitor 151 is a polarized 10-microfarad 25-volt rated capacitor with the positive terminal connected to the 5-volt output of regulator 150 and the negative terminal of capacitor 151 to the Vss bus. The +5 volt output of regulator 150 supplies+5 volts to Vdd of the microcontroller 40, to the emitter on transistor 164, to the anode of diode 175, and to the resistor 155.

The control unit microcontroller 40 can be a Microchip® PIC 16F88 microcontroller that contains internal peripheral modules consisting of an addressable analog-to-digital (A/D) converter, a Universal Synchronous Asynchronous Receiver Transmitter (USART), 16 input/output (I/O) ports and a non-volatile programmable flash memory. The particular microcontroller described is not intended to limit the use of other similar programmable devices; persons of ordinary skill will recognize that similar microcontrollers could be substituted. Details of the microcontroller program are described in flow charts shown in FIGS. 10A, 10B, 10C, and 10D. The input/output (I/O) ports that are made functional in the program consist of analog I/O ports RA0, RA1 and RA3, and digital I/O ports RB1, RB2, RB3, RB4, RB6 and RB7. Ports RA5, RB6, and RB7 are connected to the in circuit programming jack 177.

A 4.7 k ohm resistor 176 and diode 175 form a positive voltage potential to RA5. The diode 175 isolates the higher programming voltage from affecting the other electronic components in the circuit. The 5-volt positive potential is held on RA5 through current-limiting 4.7 k ohm resistor 176 to prevent a reset of the microcontroller 40 from occurring by an otherwise floating voltage potential. Port RB1 on microcontroller 40 is programmed as an I/O port to generate a digital square wave output that constitutes the stimulating micro-pulses of channel one.

A 10 k ohm resistor 160 serves as a current limiter between RB1 and the base of NPN transistor 166. The collector of NPN transistor 166 is connected to the +9 volt bus and the emitter is connected to potentiometer 169. The circuit of 100 k ohm potentiometer 169, 22 k ohm resistor 171, and 1 k ohm resistor 168 form a voltage divider and current limiter for the output of transistor 166. The Darlington transistor 173 is a current amplifier for the micro-pulsed output generated by microcontroller 40. The potentiometer 169 varies the bias voltage on the base of Darlington transistor 173. The collector of Darlington transistor 173 is connected to the step-up transformer 172. The emitter of the Darlington transistor 173 is connected to the Vss bus.

The secondary polarity point on the step-up transformer 172 is connected to the +9 volt bus. The amplified micro-pulse on the secondary of transformer 172 produces a stepped-up voltage and current output on the primary of step-up transformer 172. The transformer 172 output is connected to a power jack 174 which provides the output for the stimulus to the electrode pads 11 and 12 that will be removably attached to the user's leg. The cathode of diode 167 is connected to the +9 volt bus. The anode of diode 167 is connected to the secondary of transformer 172 and the collector of Darlington transistor 173, and forms a circuit to protect the electronic components of the control unit 10 from a high voltage kickback spike.

Port RB6 of microcontroller 40 is programmed as an I/O port to generate a digital square wave output for the stimulating micro-pulses of channel two. A 10 k ohm resistor 178 serves as a current limiter between port RB6 and the base of NPN transistor 179. The collector of NPN transistor 179 is connected to the +9 volt bus and the emitter is connected to potentiometer 182. The circuit of 100 k ohm potentiometer 182, 22 k ohm resistor 183, and 1 k ohm resistor 181 form a voltage divider and current limiter for the output of transistor 179. The Darlington transistor 185 is a current amplifier for the micro-pulsed output generated by microcontroller 40. The potentiometer 182 varies the bias voltage on the base of Darlington transistor 185. The collector of Darlington transistor 185 is connected to the step-up transformer 184. The emitter of the Darlington transistor 185 is connected to the Vss bus.

The secondary polarity point on the step-up transformer 185 is connected to the +9 volt bus. The amplified micro-pulse on the secondary of transformer 184 produces a stepped-up voltage and current output on the primary of step-up transformer 184. The transformer 184 output is connected to a power jack 186 which provides the output for stimulus to the electrode pads 13 and 14 which are removably attached to the user's leg. The cathode of diode 180 is connected to the +9 volt bus. The anode of diode 180 is connected to the secondary of transformer 184 and the collector of Darlington transistor 185, and forms a circuit to protect the electronic components of the control unit 10 from a high-voltage kickback spike. Port RB2 on microcontroller 40 is programmed as an input for the internal USART module.

The integrated circuit 45 can be an Everlight® IRM8601S infrared detector that is used to detect an asynchronous serial signal modulated by a 38 kilohertz carrier frequency. The output of infrared detector 45 is connected to I/O port RB2, configured as the input of the internal USART module of microcontroller 40, through a current limiting 10 k ohm resistor 159. The demodulated signal is received by the internal USART and decoded to a digital number used in the program. The data is transmitted by the pocket remote 30 to put the microcontroller 40 in a power-down or power-up state, or to receive programming data transmitted to the setup remote 30. A 47-ohm resistor 155 and a polarized 47 micro-ferried capacitor 157 form a filtered+5 volt potential to the input on infrared remote control receiver 45.

Port RB3 on microcontroller 40 is configured as an output to switch on the distance sensor 51. The circuit consists of a PNP transistor 164 and a currant limiting 1 k ohm resistor 163 that is connected to the base. The transistor 164 functions as a switch to apply a +5 volt potential to the input of the distance sensor 51. The distance sensor 51 can be a Sharp® GP2D120XJ00F. Persons of ordinary skill in this art, after reading this disclosure, will be able to substitute different distance sensors without departing from the scope of this invention. The analog voltage output changes as the measured distance changes. When the distance increases the analog voltage decreases. One may refer to The Sharp® reference drawing S0E005102 for details. Port RA3 on microcontroller 40 is configured as an analog A/DC input and is connected to the output of the distance sensor 51 through a 10 k ohm resistor. The analog voltage from the distance sensor 51 is converted to a digital number used in the program as described later in detail herein.

Resistor 154 is connected to port RB3 and serves as a weak pull-down resistor for I/O port RB3. Port RA1 on microcontroller 40 is configured as an analog A/D converter to monitor the battery voltage. The voltage divider circuit, comprised of a 470 k ohm resistor 152 connected to the +9 volt bus and a 300 k ohm resistor 153 connected to the Vss bus, outputs an analog voltage that changes as the battery voltage decreases. The analog voltage is converted to a digital number used in the program to determine when to generate an alarm to alert the user to a low battery voltage.

Port RA0 is configured as an analog output and is connected to piezoelectric audio transducer 43, which acts as a speaker. The speaker sounds a software-commanded tone from microcontroller 40 to alert the user to a low battery voltage and to acknowledge when data is received from the setup remote 30. Port RB4 on microcontroller 40 is configured as a digital output to send an RS232 serial signal to a test point for connecting an external liquid crystal display to diagnose software problems and to read the pulse width value, frequency value, and other values in the microcontroller 40.

Figure 8:
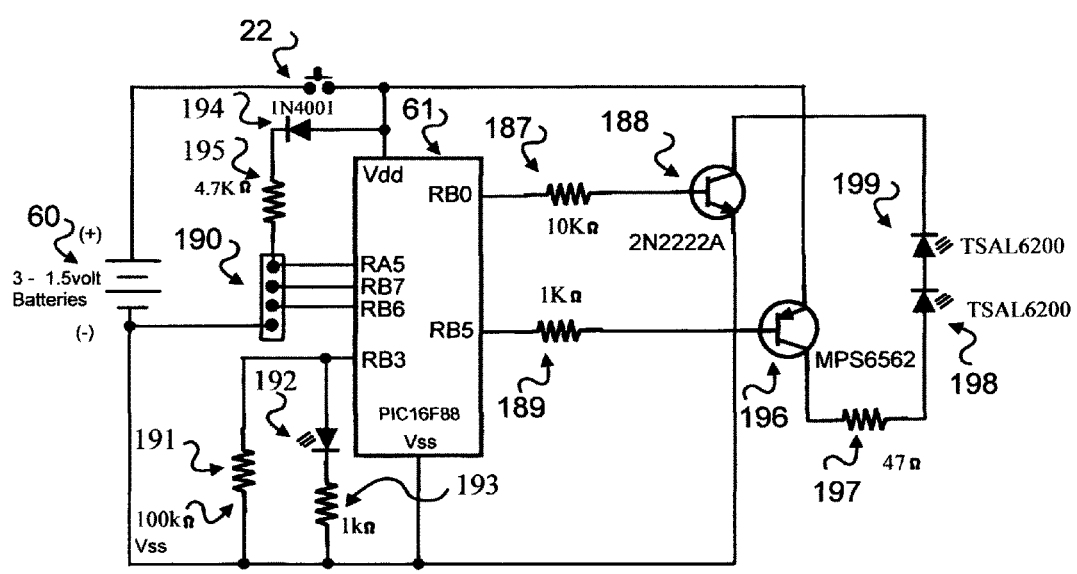
FIG. 8 is an electrical schematic diagram of a preferred embodiment of the pocket remote.

FIG. 8 is an electrical schematic of a preferred embodiment of the pocket remote 20 of FIG. 2. The 4.5-volt power is supplied by 3 alkaline button cell batteries 60 that are connected to the circuit by a push-button switch 22. When the push button is pressed, the pocket remote microcontroller 61 is connected to the Vdd bus and is energized. The Vdd bus supplies+4.5 volts to the microcontroller 61 and to the anode of diode 194. The software in microcontroller 61 begins programming the internal modules and input/output (I/O) ports. The microcontroller 61 can be a Microchip® PIC 16F88 microcontroller.

The I/O ports RB6, RB7, and RA5 of the microcontroller 61 and the Vss bus are connected to an in-circuit serial programming jack 190. A 4.7 k ohm resistor 195 and diode 194 allow a positive voltage potential to terminal RA5 of microcontroller 61. A +15-volt potential is present while the microcontroller 61 is being programmed in-circuit. The diode 194 isolates the higher programming voltage from affecting the other electronic components in the circuit. The in-circuit programming jack 190 allows the designer to reprogram the microcontroller 61 to change or add operational features to the pocket remote 20.

The microcontroller 61 is programmed to use the internal pulse width modulator (PWM) module and a Universal Synchronous Asynchronous Receiver Transmitter (USART) module. The programming sets the PWM to output a pulsed frequency of 38 kilohertz on I/O port RB0. The pulsed output of RB0 on microcontroller 61 is connected to the base of NPN transistor 188 through a current limiting 10 k ohm resistor 187. The emitter of NPN transistor 188 is connected to the Vss bus. The collector of transistor 188 is connected to the cathode of infrared light emitting diode 199. The NPN transistor 188 serves as an amplifier and switch, pulsing at 38 kilohertz. Port RB5 on microcontroller 61 is configured as the digital output for the internal module USART.

The USART transmits an asynchronous serial signal to power-down and power-up the control unit 10 as described in detail later herein. Port RB5 of microcontroller 61 is connected to a 1 k ohm resistor 189, and limits the current to the base of PNP transistor 196. The PNP transistor 196 functions as an amplifier and switch that follows the output of the USART asynchronous transmission. The emitter of transistor 196 connects to the +4.5 volt bus. The collector of transistor 196 connects to a 47 ohm current limiting resistor 197. Resistor 197 connects to the anode of infrared light emitting diode 196. The cathode of infrared emitting diode 196 is connected to the anode of infrared light emitting diode 198. The 38 kilohertz modulated data is transmitted by the infrared light emitted from light emitting diodes 198 and 199 to control unit 10. The control unit 10 decodes the serial signal and causes the unit to power-down to a low power condition or to power back on, depending on the signal received.

The infrared light emitting diodes 198 and 199 can have a light wavelength of 940 nanometers. The light wavelength emitted by LEDs 198 and 199 should match the infrared detector of the control unit 10. The anode of LED 192 is connected to port RB3 of microcontroller 61. The cathode of LED 192 is connected to 1 k ohm resistor193. The resistor 193 is connected to Vss and limits the amount of current through LED 192. LED 192 serves as an indicator and lights when the program begins in microcontroller 61. Resistor 191 is connected to port RB3 and serves as a weak pull-down resistor for I/O port RB3.

Figure 9:
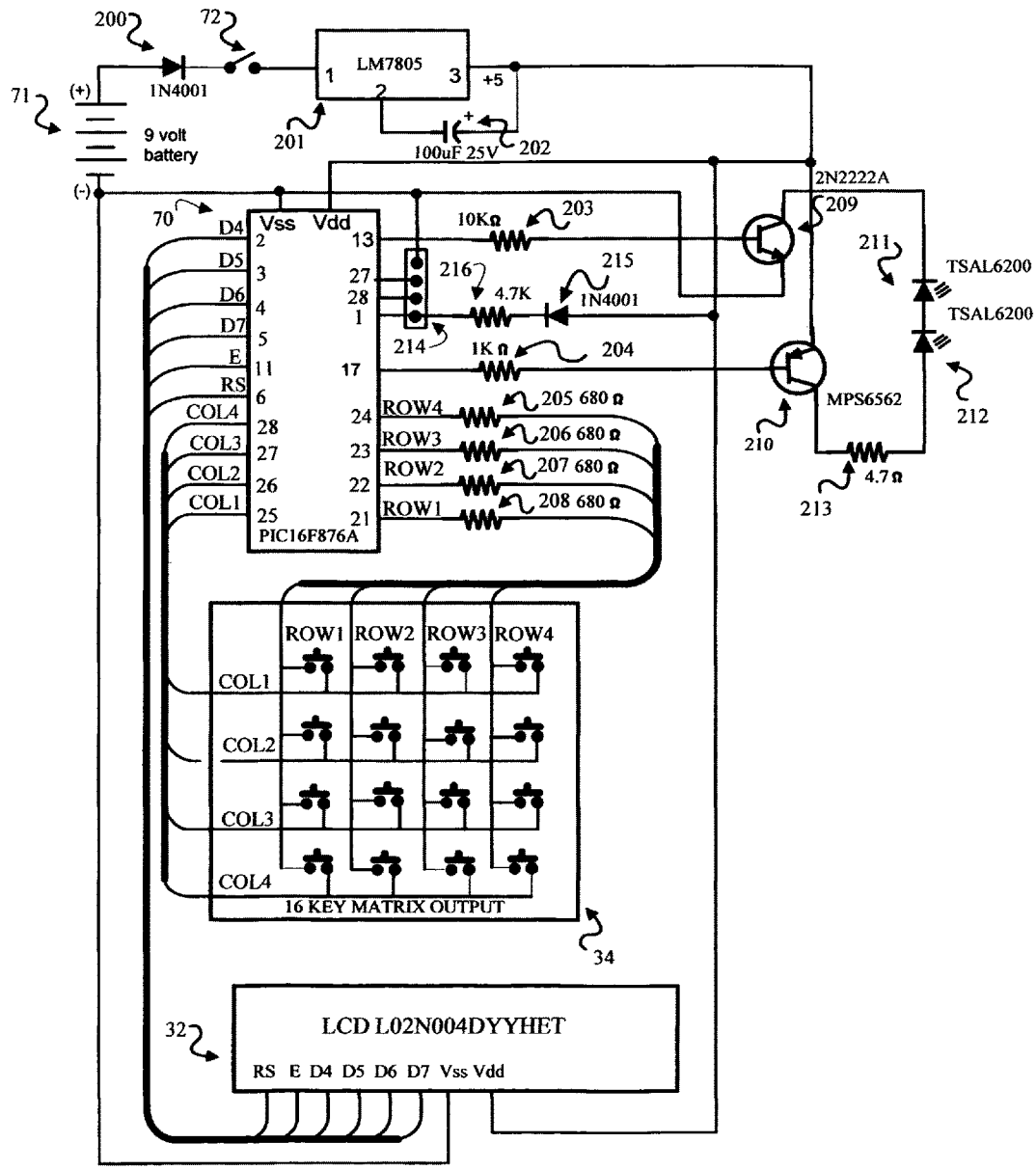
FIG. 9 is an electrical schematic diagram of a preferred embodiment of the setup remote.
Figure 10:
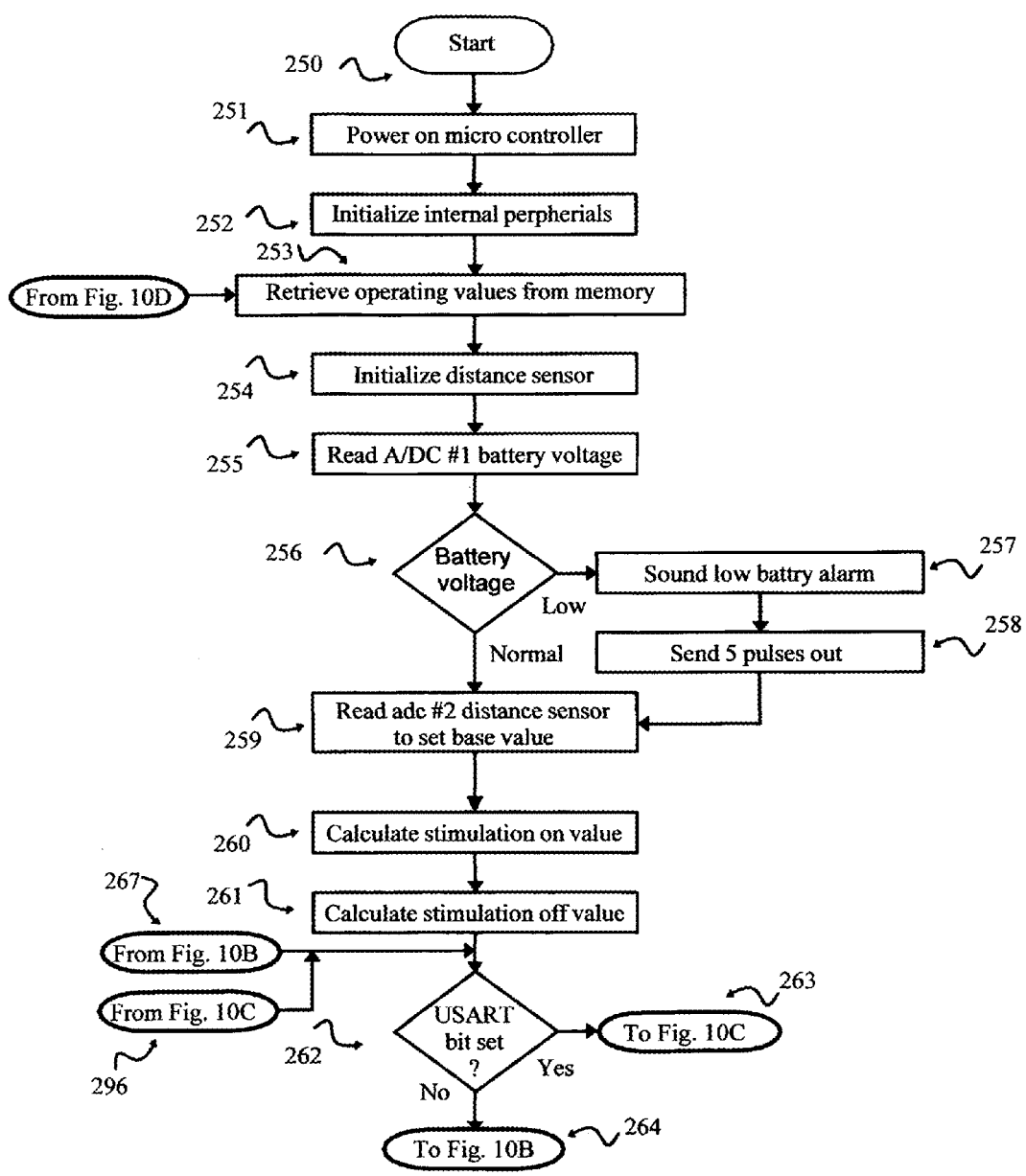
FIGS. 10A, 10B, 10C, and 10D set forth a flow chart of a preferred embodiment of the control unit.
Figure 10:
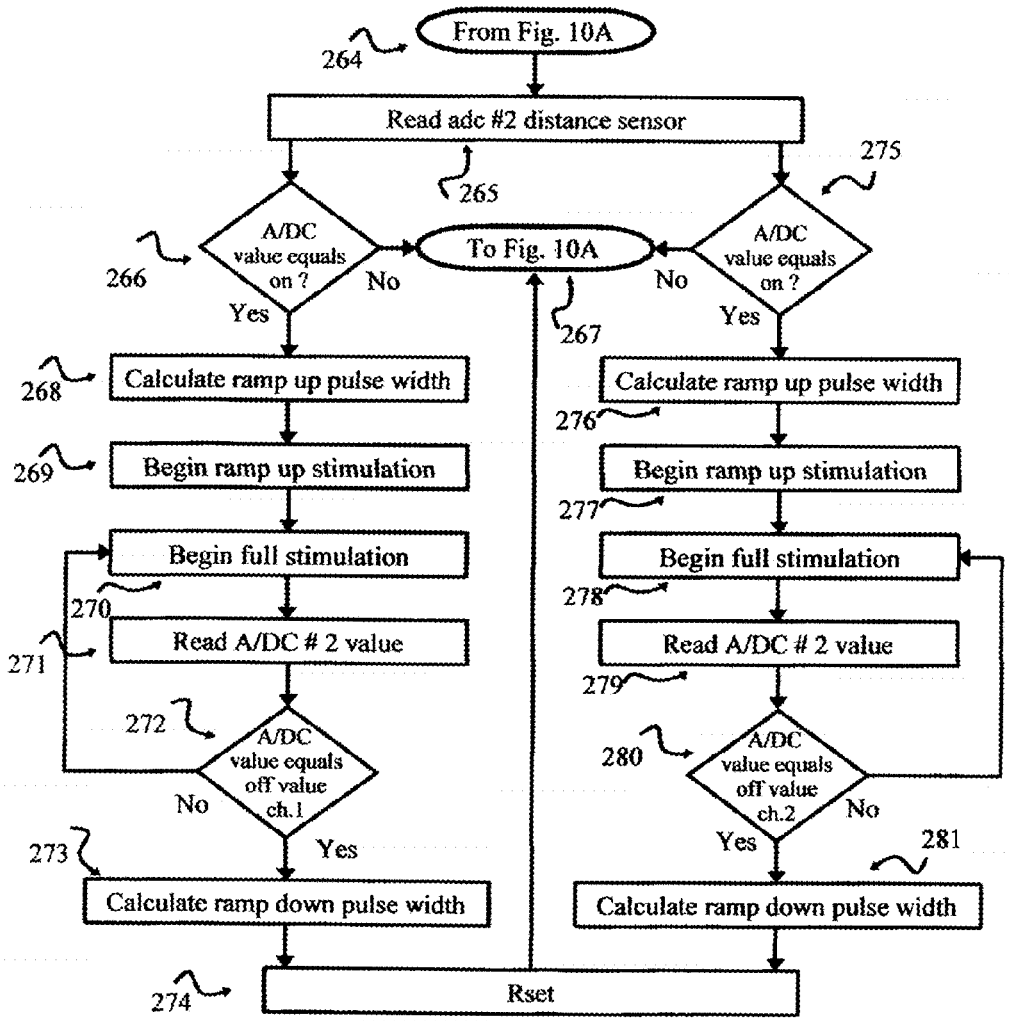
Figure 10:
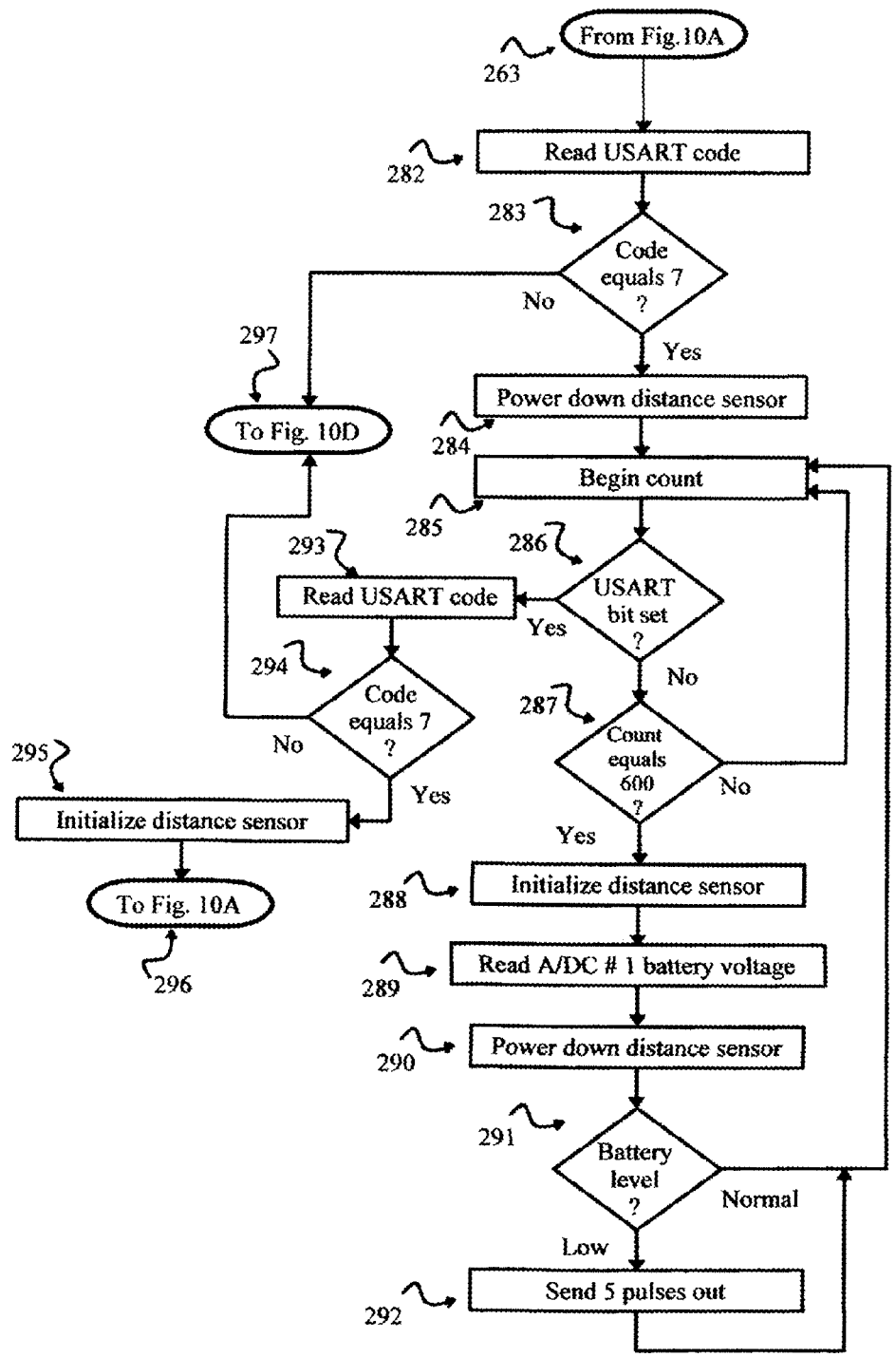
Figure 10:
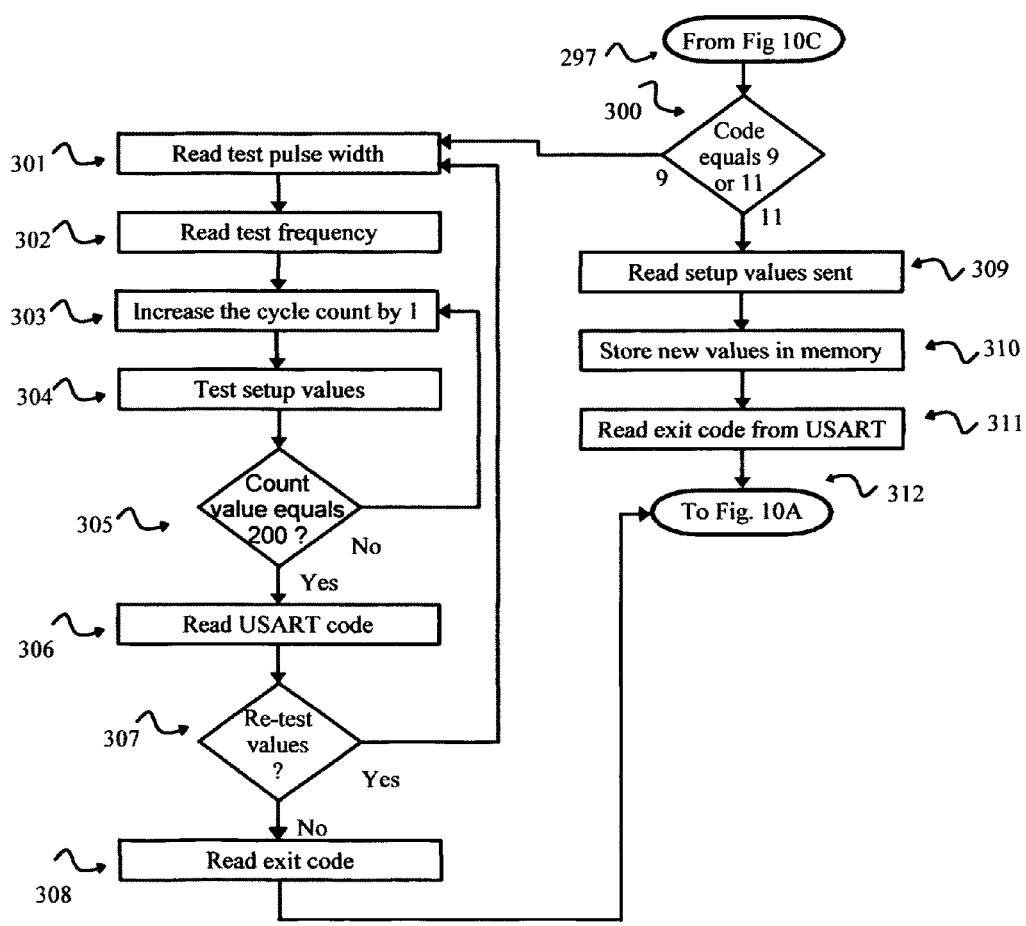

FIG. 9 is an electrical schematic of a preferred embodiment of the setup remote 30. A 9-volt alkaline or rechargeable battery 71 powers the setup remote 30 circuitry. The negative terminal of battery 71 is connected to the Vss bus, the Vss terminal of setup remote microcontroller 70, and the Vss terminal of LCD 32. The positive terminal of battery 71 is connected to the anode of diode 200. The diode 200 prevents a reverse polarity on the circuit caused by incorrectly inserting the battery 71. The cathode of diode 200 is connected to terminal 1 of the power switch 72. Terminal 2 of power switch 72 is connected to the input terminal of liner voltage regulator 201 and to the +9 volt bus of the setup remote 30 circuit. The positive (+) terminal of polarized capacitor 202 is connected to the output terminal of voltage regulator 201 and to the +5-volt bus Vdd of the setup remote 30 circuit.

The setup remote microcontroller 70 can be a Microchip® PIC 16F876A microcontroller. It has an internal pulse width modulator (PWM), an internal Universal Synchronous Asynchronous Receiver Transmitter (USART), 22 I/O ports, and non-volatile programmable flash memory. The +5-volt Vdd bus is connected to the Vdd terminal of microcontroller 70, the anode of diode 215, and the Vdd terminal of LCD 32. The I/O ports RB6, RB7, and MCLR of the microcontroller 70 and the Vss bus are connected to an in-circuit programming jack 214. The in-circuit programming jack 214 allows the designer to reprogram the microcontroller 70 to change or add operational features to the setup remote 30.

A 4.7 k ohm resistor 216 and diode 215 allow a positive voltage potential to terminal MCLR of microcontroller 70. A +15 volt potential is present while the microcontroller 70 is being programmed. The diode 215 isolates the higher programming voltage from affecting the other electronic components in the circuit. The microcontroller 70 is configured in the program to support a four-line twenty-character liquid crystal display (LCD) 32, and a four-by-four matrix sixteen-key keypad 34. The data inputs D4, D5, D6, and D7 on the LCD 32 connect to I/O ports RA0, RA1, RA2, and RA3, respectively, on microcontroller 70. The Register Select (RS) input on the LCD 32 connects to port RA4 of the microcontroller 70. The Enable Signal (E) input on LCD 32 connects to port RC0 of microcontroller 70.

The initial startup of microcontroller 70 configures the I/O outputs to be compatible with the parallel LCD 32. The sixteen-key keypad 34 consists of four rows and four columns connected in a matrix configuration. The rows 1, 2, 3, and 4 connect to four current-limiting 680 ohm resistors 208, 207, 206, and 205, respectively. The microcontroller 70 I/O ports RB0, RB1, RB2, and RB3 connect to resistors 208, 207, 206, and 205, respectively. Column 1, 2, 3, and 4 of keypad 34 connect to microcontroller 70 I/O ports RB4, RB5, RB6, and RB7, respectively. When a key is pressed on keypad 34, a row and a column are connected. The program in the microcontroller 70 determines which key is pressed, and then causes a programmed response.

The internal module PWM is programmed at the startup of microcontroller 70 to a 38 kilohertz frequency. The pulsed output of port RC2 on microcontroller 70 is connected to the base of NPN transistor 209 through a current limiting 10 k ohm resistor 203. The emitter of NPN transistor 209 is connected to the Vss bus. The collector of transistor 209 is connected to the cathode of infrared light emitting diode 211. The NPN transistor 209 serves as an amplifier and switch, pulsing at 38 kilohertz. Port RC6 on microcontroller 70 is configured as the digital output for the internal module USART. Port RC6 of microcontroller 70 is connected to al k ohm resistor 204, and limits the current to the base of PNP transistor 210. The PNP transistor 210 functions as an amplifier and switch that follows the output of the USART asynchronous transmission. The emitter of transistor 210 connects to Vdd, the +0.5 volt bus. The collector of transistor 210 connects to a 4.7 ohm current limiting resistor 213. Resistor 213 connects to the anode of infrared light emitting diode 212. The cathode of infrared light emitting diode 212 is connected to the anode of infrared light emitting diode 211.

The 38 kilohertz modulated data is transmitted by the infrared radiation emitted from light emitting diodes 211 and 212 to the control unit 10. The control unit 10 receives and decodes the serial signal that contains data values and commands to setup the operating functions of control unit 10. The infrared light emitting diodes can have a light wavelength of 940 nanometers. The wavelength emitted by the LEDs 211 and 212 should match the light wavelength capable of being detected by the infrared detector of the control unit 10.

FIGS. 10A, 10B, 10C and 10D set forth flowcharts of the preferred initialization and control routine of the preferred embodiment of the control unit 10. It is, of course, apparent that persons of ordinary skill in this art, given this disclosure, can design similar initialization and control routines which would come within the scope of this invention.

When a patient has the electrodes in place on a particular leg and the control unit 10 is securely strapped on to that leg, the patient must first stand or sit with the leg perpendicular to the surface on which the patient stands or sits. The patient is required to stay still for about a second while the control unit 10 performs the initial startup process. The program is stored in internal non-volatile flash memory of the control unit microcontroller 40.

FIG. 10A describes startup sequence flow chart for control unit 10. The flow chart of begins at step 250. The power is switched on by the switch 42 of FIG. 7 at step 251. The program routine starts initializing the internal peripheral modules that include analog-to-digital converters (A/DC) 47, 48, and USART 50 of FIG. 4 at step 252. Operating values are retrieved from internal nonvolatile memory of the microcontroller 40 at step 253. The operating values are default values unless changed by the clinician, details described later herein. The distance sensor 51 of FIG. 7 is initialized at step 253. At this step, 95 percent of operating current is now being supplied by the battery 41 of FIG. 7. Step 255 tests the battery voltage with internal analog-to-digital converter 48 of FIG. 4. The digital value is compared to the lowest accepted value in decision step 256. If the battery is low, the program is redirected to step 257. At step 258, the piezoelectric speaker 156 of FIG. 7 sounds a series of tones to alert for the low-battery condition.

Step 258 calls for five 100 micro-second pulses to be sent to the stimulus generating electrodes as a sensory alert that the patient can feel in the leg to which the electrodes are attached. The sensory alert pulses are more effective than visual or audible alerts. The environment may be too noisy to hear the tones and a visual alert may not be noticed. Low-battery voltage does not cause the shutdown of the control unit 10, but serves as a warning to the patient to change the battery. The program subroutine then returns at step 259. If the battery voltage is normal, at test 256, the next step 259 accesses the digital value from internal analog-to-digital converter 48 of FIG. 4. The distance sensor 51 of FIG. 7 generates an analog voltage that changes as the distance measured by the distance sensor changes. The digital value read from the analog-to-digital converter becomes a fixed value for the base distance that is measured from the control unit 10 to the walking surface. The base distance is the value used to calculate the distance to begin stimulus value for channel one and channel two in step 260. The distance to end stimulus value for channel 1 and channel 2 is calculated in step 261. Stimulus-on value and stimulus-off value are the points that start and stop the stimulating pulses on each channel. At step 262, the internal USART of microcontroller 40 is tested for the RCIF bit in the PIR1 register to be set. One may refer to the Microchip® PIC 16F87188 data sheet for a detailed description of the USART module. If the RCIF bit is set, a remote control subroutine is called in FIG. 10C at step 263. If the RCIF bit is not set then step 264 picks up on FIG. 10B.

FIG. 10B is a flow chart that describes the sequence of steps that begins and ends the pulsed stimulation routine of the program for channel one and channel two for the control unit 10. The stimulation routine starts at step 264 from FIG. 10A. The distance-measuring sensor to 51 in FIG. 7 outputs an analog signal that is updated approximately every 40 milliseconds. Step 265 retrieves the value from the internal analog-to-digital converter 48 of FIG. 4 to get a digital value from the distance sensor. The channel 1 decision step 266, and the channel 2 decision step 275, test the digital value every 120 milliseconds for the start-stimulus value that was previously calculated at step 260 of FIG. 10A. If the stimulus-on value for channel one or two has not been reached, the routine returns to recheck for the internal USART receive bit to be set, in FIG. 10A step 262. If the stimulus-on value for channel one has been reached, the routine moves to step 268. If the stimulus-on value for channel two has been reached, the routine moves to step 276. If channel one starts first, step 268 calculates the ramp-up value by using the set pulse-width value read from memory at step 253 from FIG. 10A. Ramp-up is a train of increasing pulse widths at a calculated value derived from the number of the cycle value stored in memory. At step 269, during each cycle, the ramp-up pulse width increases at a percentage of the stimulus pulse width that was read from memory. As the pulse width increases, the stimulus intensity increases, causing the foot to gradually lift.

Step 270 begins the full stimulation output with the pulse width value retrieved from memory. The pulse width value sets the length of time the microcontroller outputs a digital 1 or "on" signal at port RB1. The frequency value retrieved from memory sets the length of time port RB1 is a digital 0 or off. During the off-time of the stimulus cycle, the analog-to-digital converter 48 reads the analog value of the distance sensor 51 in step 271. Step 272 tests the digital distance sensor value to determine whether the stimulus-off value has been reached. If the stimulus-off value has not been reached, the routine starts over at 270. The cycle continues until the stimulus-off value is met. The routine moves to step 273 and calculates the ramp-down value of the pulse width. The ramp-down calculation process is the same as the ramp-up calculation process. The ramp-down pulse width gets smaller in each cycle, gradually lowering the foot until the ramp-down stimulus ends. Step 274 resets all values to 0 and sends the routine back to FIG. 10A step 262 to restart the process.

The control unit 10 is a dual-channel stimulator designed to stimulate two muscle groups. The stimulation on each channel begins and ends at different points in the walking cycle. These points are determined by the location of the foot. The output of channel two is active while the output of channel one is in the off portion of the stimulus cycle. The output of channel one is active while channel two is in the off portion of the stimulus cycle. The off time of each channel overlaps with approximately 24 milliseconds of lapsed time. The distance sensor is checked while both channels are in the off portion of their stimulus cycles. The two channels appear to stimulate simultaneously but actually alternate the stimulus cycle. The stimulus routine of channel one is the same as channel two.

FIG. 10C is flow chart of the remote control subroutine that causes the control unit 10 to be in the standby mode. The standby mode causes the power consumption to be 95 percent lower. The battery voltage is checked every two minutes while in standby. On FIG. 10A step 262 checks for the RCIF bit of the PIR1 register to be set. If it is set, the remote control subroutine of FIG. 10C begins. The pocket remote 20 transmits the code number 7 that is received by the USART module in microcontroller 40. Step 282 of FIG. 10C reads the code. If the code does not equal 7, the decision step 283 sends the routine to FIG. 10D. If the code equals 7, the routine begins setting up the standby mode for the FES Unit 10. The distance sensor 51 of FIG. 7 is switched off at step 284. Step 285 sets up a counter that acts as a timer. The counter is advanced by one each time the routine returns to step 285. The USART is checked for the RCIF bit of the PIR1 register to be set at step 286. If the bit of the USART is set the routine moves to step 293. If the RCIF bit of the PIR1 register is not set, the routine is put into a loop that increases the count by one at step 285 and checks for the USART receive bi to be set at step 286.

Decision step 287 checks the count until it equals 600, which equates to approximately two minutes. Step 288 initializes the distance sensor 51 to put the battery back under normal load condition. Step 289 accesses the internal analog-to-digital converter 47 of FIG. 4 to get a digital value of the battery voltage. Step 290 turns the distance sensor off and moves to step 291 to check the battery voltage level. If the voltage is in the normal range, the loop is started over at step 285. If the battery voltage is low, a train of five 100 micro pluses is sent to the stimulus electrodes to cause a sensory alert to the patient. Then the standby loop is started over at step 285. During the standby loop, step 286 checks the USART for the RCIF bit of the PIR1 register to be set. When receive bit is set at step 286, the routine is moved to step 293 to read the code transmitted by the pocket remote 20. Decision step 294 checks the code. If the code equals 7 the distance sensor in energized in step 295. At step 296, the subroutine is directed to FIG. 10A to start the control routine at step 262. If the code does not equal 7 at step 294, the subroutine moves to the setup flow chart 10D, at step 297.

FIG. 10D illustrates a flow chart of a preferred embodiment of the control unit 10. The program of control unit 10 uses various values that are stored in the non-volatile memory of control unit microcontroller 40 of FIG. 7. Default values and program instructions are loaded into microcontroller 40 to begin using the control unit 10. The clinician can change the default values by using the setup remote 30, to set values to fit any individual patient. FIG. 10D describes the program flow chart, when the setup remote 30 has transmitted a command or operating values to the control unit 10. FIG. 10C decision step 283 and 294 have checked the code received by the internal module USART of microcontroller 40 and it did not equal 7. The routine is directed to step 297 of FIG. 10C. Decision step 300 directs the subroutine to test the pulse width and frequency values if the code equals 9, or to set all the values if the code equals 11. If the code equals 9, the control unit 10 is set to allow the clinician to change and test the pulse width and frequency values of channel 1 and or channel 2. The clinician tests various pulse width and frequencies to find the optimal stimulus pulses for the patient. As the pulse width increases the stimulus pulse causing the stimulus output to get stronger. A stronger stimulus causes the muscle increase in strength. The pulse width and frequency values are transmitted by the USART of the setup remote 30.

At step 301, the pulse width values are retrieved from the USART receive register. At Step 302 the frequency value is retrieved from the USART receive register. At step 303 the routine sets up a counter that begins at one. Then, at step 304, the pulse width and frequency values are tested by outputting a train of stimulating pulses at the new test values. Decision step 307 checks the cycle count number to equal 200. If the condition is not true, the routine loops back to step 303 and increments the cycle count number by one. The stimulus lasts about six seconds at a cycle count of 200. When the cycle count equals 200, the routine ends the stimulating pulses to the user. Then, the routine waits at step 306, for the USART to receive a new command code. When the new command code is received by the USART, decision step 307 loops the routine to return to step 301 to retest new values; or to save the new pulse width and frequency values, exit the setup routine, at step 312, and return to the startup routine at step 253 of FIG. 10A.

Decision step 300 directs the program routine to step 309 if the code received by the internal modular USART of microcontroller 40 equals 11. The clinician enters specific operating values in the setup remote 30. The values consist of pulse width, frequency, ramp-up, ramp-down, and the stimulus-on and stimulus-off percent values that are the correct parameters for the individual patient. The values and the command to store the values in memory are transmitted by the internal USART module of microcontroller 70 of FIG. 9. Step 309 retrieves the values from the USART receive register and at step 310, the values are stored in non-volatile memory in microcontroller 40. The code to exit the setup subroutine is received at step 311. The subroutine ends at step 312 and is directed to the startup routine FIG. 10 at step 253.

Figure 11:
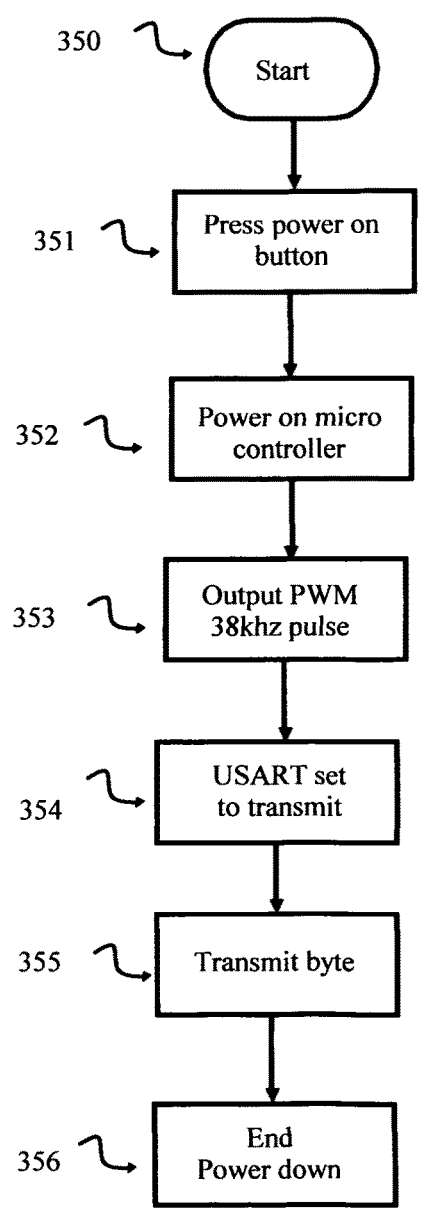
FIG. 11 sets forth a flow chart of a preferred embodiment of the pocket remote.

FIG. 11 describes a program flow chart of a preferred embodiment depicting the functions of the pocket remote 20. The pocket remote 20 is used by the patient by pressing button 22 to put the control unit 10 in standby. While in standby, the current load on the control unit 10 battery is reduced by 95 percent. The patient can put the control unit 10 back in use by pressing button 22 on the pocket remote 20.

Step 351 begins with the pocket remote 20 being powered on by push button 22. At step 352, the microcontroller 70 internal pulse width modulator (PWM) and USART peripherals are initialized. The routine steps to 353 and starts the internal pulse width modulator module to output a modulated frequency at 38 kilohertz. Step 354 sets the internal USART module to transmit an asynchronous serial signal. Step 355 loads a pre-set value in the USART transmit register. The value is sent out as an asynchronous serial signal that is modulated using the internal PWM module for the 38 kilohertz carrier frequency. See the electrical schematic FIG. 8 for further explanation. The program ends at 356. The push button 22 in FIG. 2 must be pressed again to repeat the process.

Figure 12A:
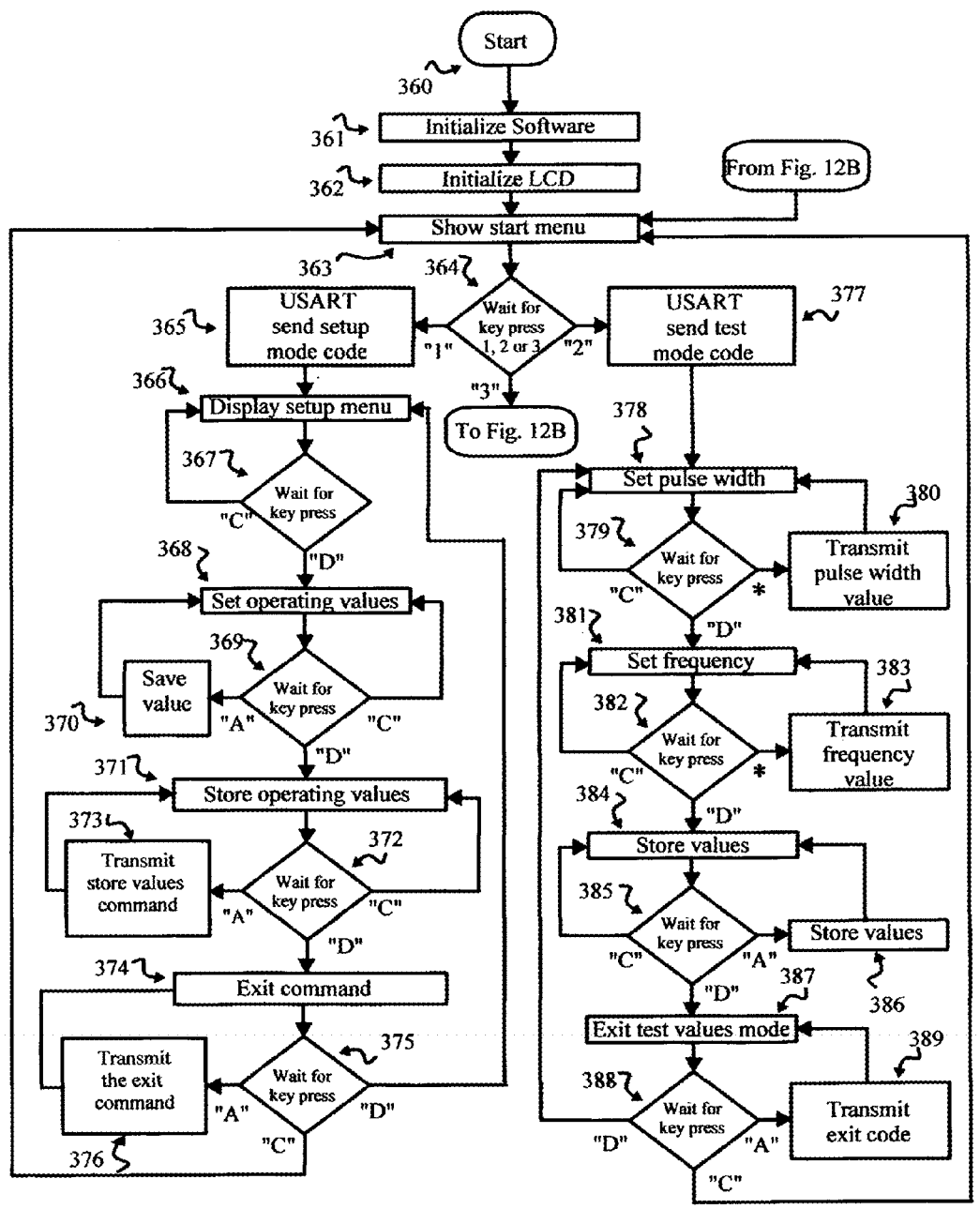
FIGS. 12A and 12 B set forth a flow chart of a preferred embodiment of the setup remote.
Figure 12B:
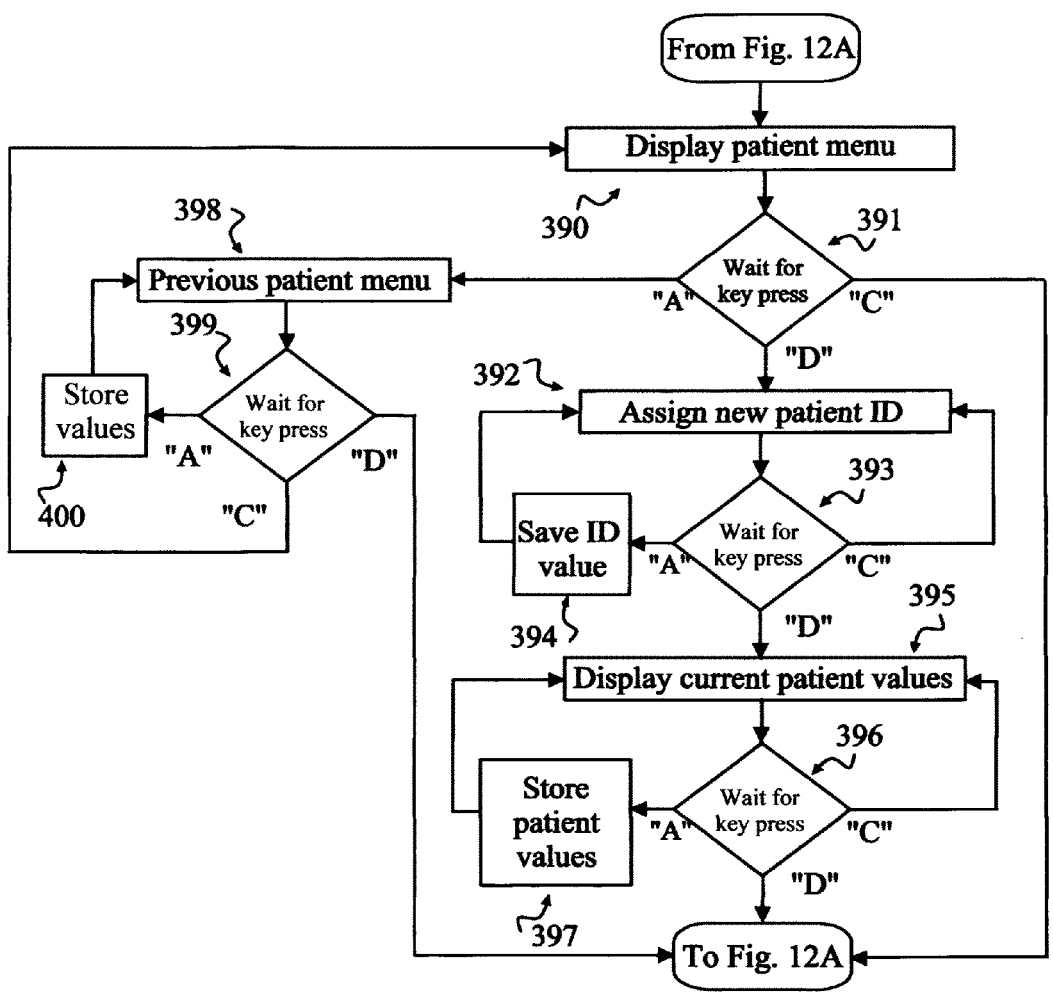

FIGS. 12A and 12B are the flow charts for the program of the setup remote 30 of FIG. 3. The control unit 10 can be factory-programmed with default operating values and parameters. Operating values are those variables that the program of control unit 10 uses to cause the unique stimulus pulse width and frequency stimulus that meet the specific requirements of the patient. The setup remote 30 is a wireless remote control unit that is menu-driven with choices for the clinician to change the operating values. These values include the pulse width and frequency of the stimulus used to lift the foot. Other values include the ramp-up and ramp-down stimulation that causes a gradual lifting and lowering of the foot. The setup remote 30 transmits the data by the internal USART module that sends an asynchronous serial signal using infrared light emitting diodes. The control unit 10 receives the data and commands as described in the flow charts of FIG. 10 and its accompanying description.

The setup remote 30 can use a Microchip® PIC 16F876A microcontroller that has internal peripherals that include a pulse width modulator (PWM) and a Universal Synchronous Asynchronous Receiver Transmitter (USART) module. The setup remote 30 uses a sixteen-key keypad 34 and a four-line by twenty-character liquid crystal display (LCD) 32 of FIG. 3.

FIG. 12A begins at step 360 when the power switch 72 of FIG. 9 is switched on. The software is initialized, setting the internal module values and software variables at step 361. Step 362 initializes the LCD 32. The menu is displayed at step 363. The clinician is instructed to choose one of three functions that are displayed in the menu. The routine loops until the number is pressed on the keypad 34 that represents one of the choices on the menu. The decision step 364 causes the routine to go the set values subroutine if the number 1 is pressed. If the number 2 is pressed, the routine goes to the test values subroutine. By pressing the number 3, the subroutine starts at the patient records menu.

Although this disclosure envisions a clinician as being the person who will typically choose the operating values for the control unit 10 by operating the setup remote, any other person could do this, including the patient. Further, the particular routines and subroutines disclosed here are merely those of the preferred embodiment. Persons of ordinary skill in this art, having read this disclosure, will be able to provide other routines and subroutines without departing from the scope of this invention.

Menu choice number 1 allows the clinician set the operating values of control unit10. At step 365 the USART transmits a code to put the control unit 10 in the setup values subroutine. The setup menu is displayed in step 366. Decision step 367 waits for a key to be pressed. The choices are associated with the keypad numbers and letters. The options include the letter "C" for cancel and return to step 366, or press the letter "D" and drop down to the next menu at step 368. The pulse width menu gives the option to enter numeric values from the keypad to set the pulse width. The three command choices are also displayed on the LCD. Decision step 369 waits for the clinician to press letter "A" and save the value at step 370, "D" to step down to the next menu at step 371, or press "C" to cancel the pulse width number and re-enter the numeric value at step 368. If the clinician chooses to save the pulse width value at step 370 the routine stores the value in the RAM of the control unit microcontroller 70, then moves to step 368 to start over with the same menu choices. When the clinician is ready, the letter "D" is pressed to step down to the next menu display. The process repeats the same steps to enter all the setup values for the control unit 10.

When the values for all the operating parameters are saved in RAM, the routine moves to step 371, the store menu. The decision step 372 gives the clinician the choice to press "A" and transmit the saved parameter values to the control unit 10 and replace the default values in the internal non-volatile memory of microcontroller 40, or press "D" to step to the exit menu, step 374. If "A" is pressed, the USART of setup remote microcontroller 70 transmits the asynchronous serial data that contains the values and the store command to the control unit 10. The routine loops back to step 371 to give the clinician the choice to repeat the save command or to press "D" to move to the next menu. Step 374 displays the exit menu with three choices. The decision step 375 waits for the clinician press a key. If the clinician presses "A" to exit the routine, the USART in microcontroller 70 sends the asynchronous serial data that causes the control unit to leave the remote control subroutine, described in FIG. 10D. If the clinician presses "D", the routine moves back to step 366 that allows the clinician to repeat the setup process, or by pressing "C" the routine begins at step 362 displaying the start menu.

The start menu option number 2 allows the clinician to test pulse width and frequency values on the patient to determine the optimal values for lifting the foot and to find the correct electrode placement over the nerve and muscle. When menu option number 2 is chosen, decision step 364 directs the routine to the test values subroutine. At step 377, the USART in microcontroller 70, transmits the asynchronous serial data that contains the command to start the test values subroutine in the control unit 10. The pulse width menu is displayed at step 378. Decision step 379 waits for the pulse width numbers to be entered from the keypad 34. The clinician can choose one of three commands from the menu. If the letter "C" is pressed the subroutine is directed back to step 378 to re-enter the pulse width numbers. Pressing the letter "D", causes the subroutine to move to the set frequency step 381.

To test the pulse width, the clinician presses the "star" key that causes the USART module of microcontroller 70 to transmit the pulse width values and command code 9 to the control unit 10 to initiate the test pulse width subroutine of FIG. 10D. The subroutine loops back to step 378 to allow the clinician to enter new values and retest the pulse width, or to move to the frequency test menu at step 381. The frequency test menu is displayed at step 381. Decision step 382 waits for the frequency numbers to be entered from the keypad 34. The clinician can choose one of three commands from the menu. If the letter "C" is pressed the subroutine is directed back to step 381 to re-enter the frequency numbers. Pressing the letter "D", causes the subroutine is move to step 384, to the store values menu. To test the frequency values, the clinician presses the "star" key that causes the USART module of microcontroller 70 to transmit the frequency values and the command code 9 to the control unit 10 to initiate the test pulse width and frequency subroutine of FIG. 10D. The subroutine loops back to step 381 that allows the clinician to retest the frequency values or move to the store values menu at step 384.

The store values menu displays three options that allow the clinician to store the frequency and pulse width values, to cancel and return to the store values menu, or to step down to step 387, the exit test menu. At decision step 385, if the letter "A" is pressed, the subroutine moves to step 386 that stores the frequency and pulse width values in the RAM of microcontroller 70. The routine loops back to the store values menu at step 384. Pressing the letter "D" causes the subroutine to move to step 387, the exit test values menu. The exit test menu displays three options. The clinician can press "D" to loop back to the set pulse width menu at step 378, press "C" to return to the start menu at step 363 or press "A" to transmit the exit code to control unit 10. At decision step 388, if the letter "A" is pressed on keypad 34, the subroutine is directed to step 389. The internal USART module of microcontroller 70 is initialized, and the exit code is transmitted to the control unit 10. The subroutine of the control unit 10 reads the exit code at step 308 of FIG. 10D and allows the control unit 10 to move out of the test values mode. The setup remote 30 subroutine loops back to the exit menu allowing the clinician to repeat the exit routine, to return to the test pulse width routine at step 378, or leave the test values mode and return to the start menu at step 363.

FIG. 12B describes the flow chart of the setup remote 30 patient record storage and recall. If menu option 3 of decision step 364 of FIG. 12A is chosen the patient records subroutine begins at step 390. The patient menu is displayed on the LCD 32. The decision step 391 waits for the clinician to press a key. If the "A" key is pressed the previous patient records subroutine begins at step 398. Option "C" causes the subroutine to return to the start menu at step 363 of FIG. 12A. If all the values of a new patient have been stored in RAM of microcontroller 70, option "D" is selected. The subroutine moves to step 392 to allow the clinician to assign a patient identification number. The clinician enters a unique ID number that represents the patient. At decision step 393, the clinician can press "C" to loop back to step 392 and change the ID number. If "A" is pressed the patient ID number is stored in RAM of microcontroller 70. Once the ID number is entered and stored the clinician is allowed to press "D" and move to step 395. The current patient operating values, stored at step 370 of FIG. 12A, are retrieved from RAM and are displayed on the LCD display 32. At decision step 396, the clinician can choose to save the patient's operating values by pressing the "A" key, or press "C" to return to the patient menu at step 390, or press "D" to leave the patient records mode and return to the start menu at step 363 of FIG. 12A. When the clinician presses "A" on keypad 34, the patient's ID and operating values are stored in non-volatile memory in microcontroller 70 at step 397.

If the clinician needs to recall an existing patient's operating values, the letter "A" is pressed at step 391. Existing patient ID and associated operating values may be retrieved at step 398. Decision step 399 gives the clinician the option to enter an ID number and display the operating values on the LCD 32, press "C" to loop back to step 398 to retrieve another ID and operating values, or save the current values to RAM at step 400. When the operating values are stored in RAM, the clinician can press "D" and return to step 363 of FIG. 12A. The operating values stored in RAM can be transmitted by the USART to the control unit 10, by returning to the setup menu of FIG. 12A at step 373.

Explanation of the FES Function During Walking

The manner in which this invention functions will be described in two typical scenarios. In the first scenario, the person will start by from a still position with both feet on the ground generally adjacent each other and both legs generally perpendicular to the ground. The person will take one step forward with each leg, and then stop with both feet again generally adjacent each other and both legs generally perpendicular to the ground. This first scenario is illustrated in the timing diagram shown in FIG. 13.

In the second scenario, the person is already walking forward at a normal rate. The scenario begins when the right leg is on the ground and the right leg is generally perpendicular to the ground, and the left leg is slightly lifted and is swinging forward in the process of stepping at the point where the left foot is generally adjacent, but slightly higher than, the right foot. In this scenario, the person is continually walking and one complete step of each foot is described. This second scenario is illustrated in the timing diagram shown in FIG. 14.

For the purpose of description, in both scenarios, the right leg is wearing the control unit and stimulation occurs to the right leg. The left leg has no stimulation. Of course, in practice, either leg or both legs can wear the control unit and be stimulated by individual FES stimulators.

Figure 13:
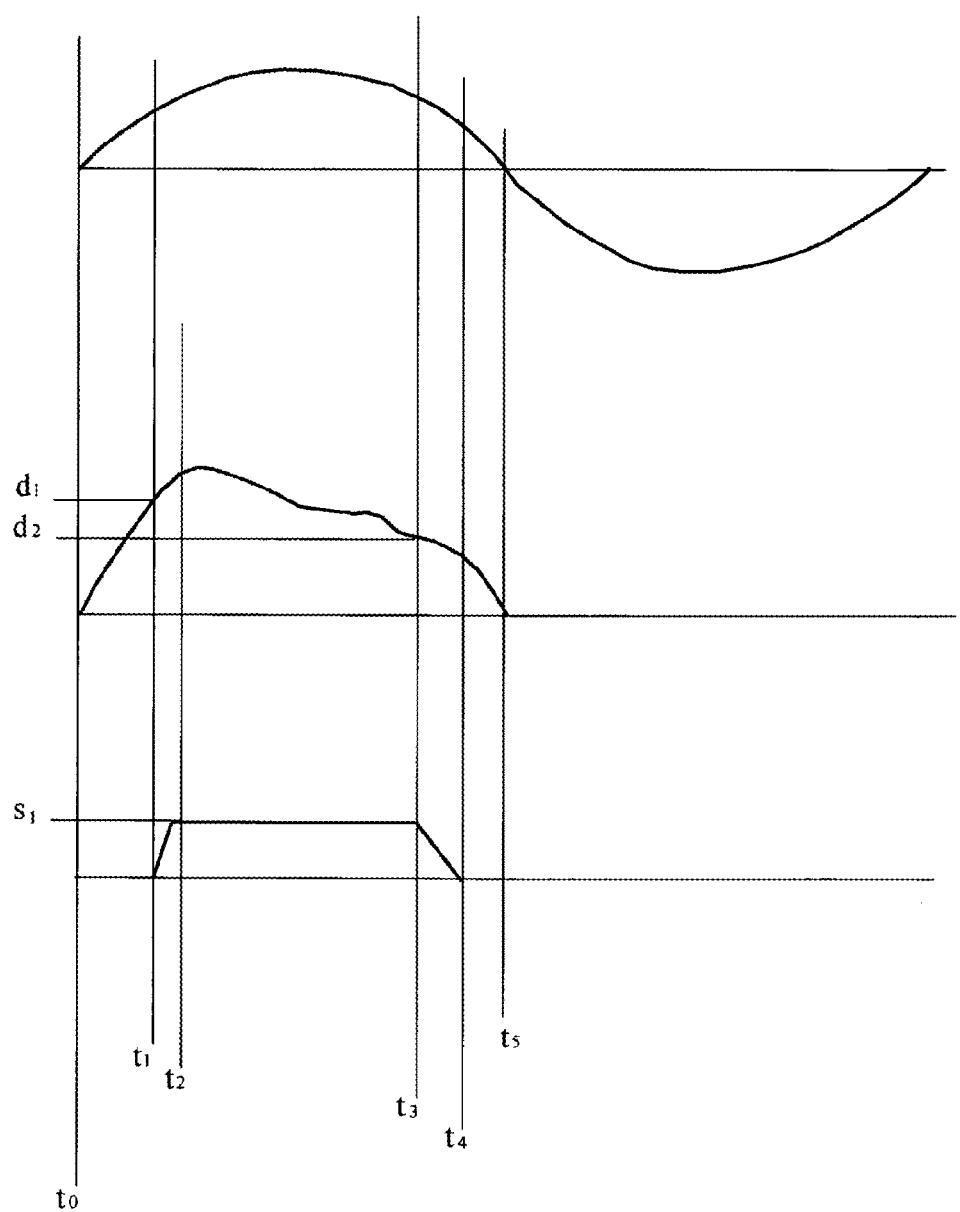
FIG. 13 is a timing diagram of a preferred embodiment that explains operation of the FES device during one complete step.
Figure 14:
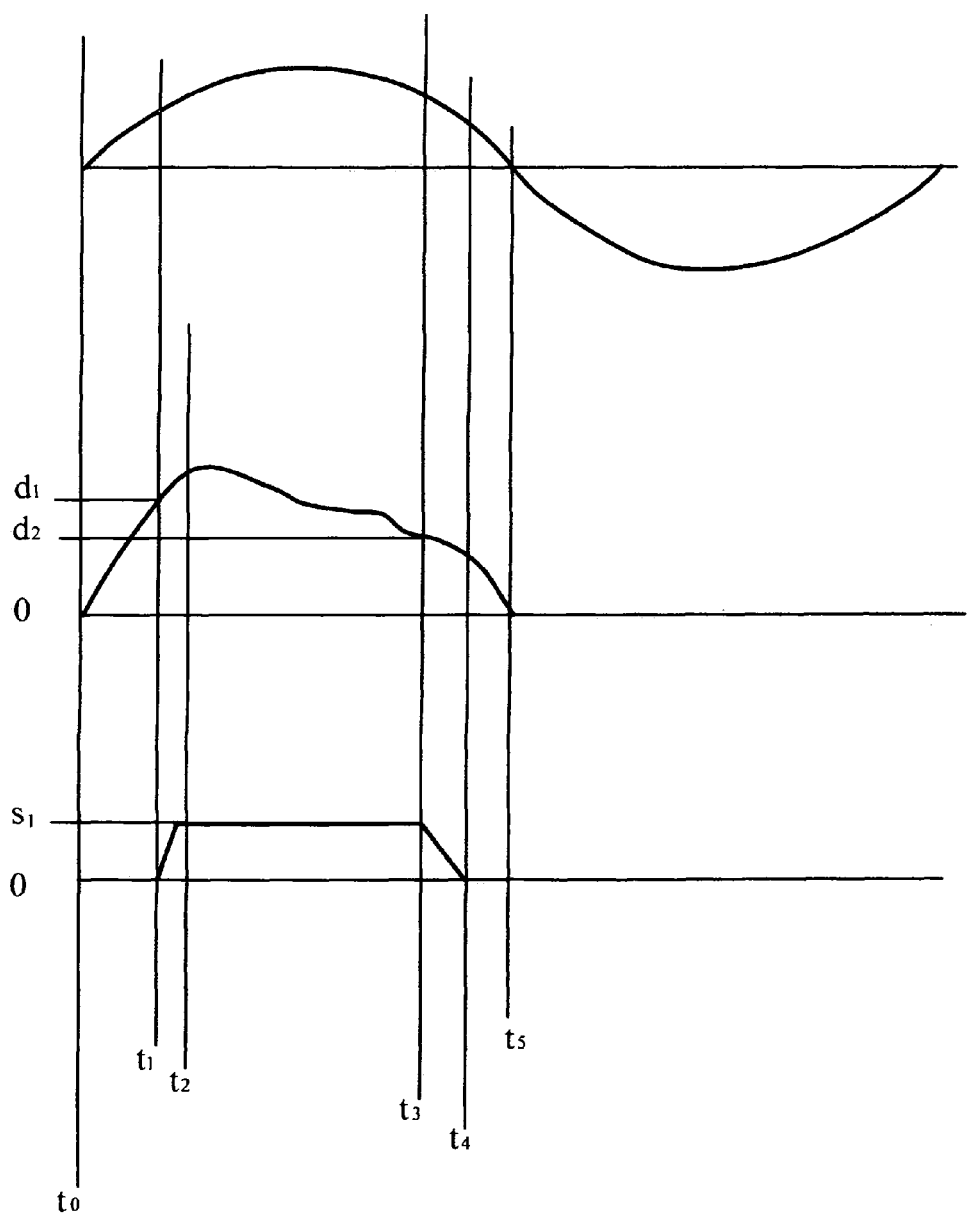
FIG. 14 is a timing diagram of a preferred embodiment that explains operation of the FES device during continuous walking.

In the timing diagrams of FIGS. 13 and 14, the top axis is an arbitrary sine wave that represents a full step with each leg of the person. The middle axis shows the distance between the control unit on the person's right leg and the ground, as measured by the control unit. The lower axis shows the level of functional electrical stimulation applied to the person's right leg as commanded by the control unit.

It should be understood that the distance displayed on the middle axes of the figures is merely an example that might result from a particular person's walking gait. It is for illustrative purposes only. Different people and different walking gaits will produce different waveforms. Persons of ordinary skill will be able to comprehend this invention from the illustrated waveform and will be able to apply this invention to any person's gait.

In both scenarios, the control unit has already been switched on, all operative factors have been programmed, and initialization has already occurred.

1. First Scenario

The timing diagram of FIG. 13 describes the function of the preferred embodiment. The top figure is an arbitrary sine wave that represents a full step starting with the person wearing this invention standing completely still. In this description, the person has already switched the invention on and calibration has occurred. The person is ready to walk forward. At time $t_0$, the person is standing still with both legs generally perpendicular to the ground and feet generally adjacent to each other. At that time, the person begins the process of taking two steps after which the person will come to a complete stop with both legs generally perpendicular to the ground and feet generally adjacent to each other.

For the purposes of this description, the person wears this invention on the right leg and does not have a stimulator on the left leg. At time $t_0$, the person begins the first step by swinging the left leg forward. As the left leg swings forward, the right leg (which wears the invention) tilts forward at the ankle, increasing the distance between the control unit and the ground.

As the person swings the left leg forward, bending it at the knee, the person's body moves forward. The left foot is then placed on the ground one step away from the starting position, at which time the right leg is tilted forward. At time $t_1$ during the step forward, the distance between the control unit and the ground, as measured by the measuring means of the control unit, reaches and exceeds a first predetermined distance. When the distance equals the first predetermined distance, the control unit causes the FES stimulator to begin stimulating the person's right leg. The particular first predetermined distance is set for each particular user by the clinician using the setup remote 30. Stimulation is ramped up at a rate predetermined by the clinician and entered into the microcontroller from the setup remote. At time $t_2$, stimulation has completely ramped-up and remains constant at signal level $s_1$ until time $t_3$. Stimulation can take any suitable form, as is discussed elsewhere. Stimulation can immediately begin at full power, but it is preferable to have stimulation ramp up in power over a relatively short time period. Once full stimulation power is reached, it is preferably kept generally constant, although it can be made to vary in intensity during stimulation.

Stimulation of the right leg continues while the right leg is lifted up slightly and begins its swing forward. Stimulation causes the right foot to be tilted up, thereby preventing the drop-foot problem. The person swings the right leg forward. As the right leg swings forward, the right foot passes the left foot which is placed on the ground. The person's body moves forward and the right foot is placed on the ground.

At a time $t_3$, which occurs between the time the right foot passes the left foot and the time the right foot is placed on the ground, the distance between the control unit and the ground decreases to a second predetermined distance. The second predetermined distance, $d_2$, is less than the first predetermined distance $d_1$. When the second predetermined distance is reached, the control unit commands the FES stimulator to begin a fixed ramp-down of the stimulation applied to the right leg. The time period during which ramp-down of the stimulation occurs is preferably greater than the time period during which ramp-up of the stimulation occurs. Ramp-down of stimulation ends at time $t_4$.

As the right foot is placed on the ground, the person's body moves forward and begins to slow. At time $t_5$, the person's right leg is again generally perpendicular to the ground. The person completes this example of steps by lifting the left foot off the ground, swinging the left leg forward, and placing the left foot on the ground generally adjacent the right foot. The person has thus taken one step with each foot in this example.

Various factors of this process can be programmed at various levels. The first and second predetermined distances can be set at any desired level which produces effective walking for the person. The first predetermined distance will always be set at a greater level than the second predetermined distance. The time period for ramp-up of stimulation and the time period for ramp-down of stimulation can be set to any suitable time periods. The time period for ramp-up will usually be shorter than that for ramp-down.

2. Second Scenario

In this second scenario, the person is already walking forward at a normal rate. The control unit is secured to the person's right leg and was initialized before walking commenced. This scenario is illustrated in the timing diagram of FIG. 14. The scenario begins at time $t_0$ when the right leg is on the ground and the right leg is generally perpendicular to the ground, and the left leg is slightly lifted and is swinging forward in the process of stepping at the point where the left foot is generally adjacent, but slightly higher than, the right foot. At this point also, the person's body is moving forward at a normal walking rate. In this scenario, the person is continually walking and one complete step of each foot is described. The person does not start or stop in this scenario's description.

As the person's left leg swings forward past the perpendicular, the person's body begins to move forward of the right foot's location on the ground. The right leg begins to tilt forward and the distance between the control unit and the ground increases. When the person has stepped sufficiently forward, the left foot is placed on the ground. At time $t_1$ during the step forward, the distance between the control unit and the ground, as measured by the measuring means of the control unit, reaches and exceeds a first predetermined distance, $d_1$. When the distance equals the first predetermined distance, the control unit causes the FES stimulator to begin stimulating the person's right leg. Stimulation causes the person's right foot to tilt upwards, thereby avoiding drop-foot problems. Stimulation ramps-up from zero to signal level $s_1$ from time $t_1$ to $t_2$.

After the person has placed the left foot on the ground, the right foot leaves the ground and the right leg swings forward. Stimulation of the right leg keeps the right foot tilted upwards. The slightly elevated right foot then passes the left foot, which is on the ground, and moves forward to be placed on the ground. After taking a normal step, the right foot is placed on the ground and the person's body begins to place its weight on the right foot.

At a time $t_3$, which occurs between the time the right foot passes the left foot and the time the right foot is placed on the ground, the distance between the control unit and the ground decreases to a second predetermined distance, $d_2$. The second predetermined distance, $d_2$, is less than the first predetermined distance, $d_1$. When the second predetermined distance is reached, the control unit commands the FES stimulator to begin a fixed ramp-down of the stimulation applied to the right leg. The time period during which ramp-down of the stimulation occurs is preferably greater than the time period during which ramp-up of the stimulation occurs. Ramp-down is shown from $t_3$ to $t_4$ in FIG. 14.

After the right foot is placed on the ground, the left foot is lifted off the ground and again begins to swing forward for another left-foot step. As this scenario ends, the left foot is swinging forward and, without stopping, reaches the point generally adjacent the right foot and slightly above it. Thus, this scenario has described one full step for each foot during a normal walking gait.

3. Reasons for Ramp-Up and Ramp-Down

Electrical stimulation of human muscles causes fatigue in those muscles stimulated. It is desirable in designing a functional electrical stimulation system to minimize the amount of time that stimulation is applied so as to minimize muscle fatigue. This invention is advantageous because it minimizes the time spent stimulating muscles during walking, thereby reducing fatigue of the muscles and increasing the amount of time that the person can walk. This invention minimizes fatigue by beginning ramp-up of stimulation after the foot leaves the ground when beginning a step, as opposed to when the person's heel leaves the ground. Likewise, this invention minimizes fatigue by beginning ramp-down of stimulation before the person's foot is placed on the ground at the end of a step, as opposed to when the foot is on the ground.

It is also not desirable to immediately start and immediately stop stimulation. Rather, it is more desirable to ramp-up the stimulation applied to the muscles when beginning stimulation, and to ramp-down the stimulation when ending stimulation. Ramping-up and ramping-down stimulation gives a more natural movement to the affected foot, and a better walking cadence. It may also be less tiring on the muscles.

CONCLUSION

The applicant has provided a particular preferred embodiment in substantial detail. However, the invention is not limited to the details of the preferred embodiment. Instead, the teachings herein may be used by persons of ordinary skill in this art to make other embodiments and equivalents that are within the scope of this invention as set forth in the claims below. This invention is limited only by the applicant's claims.

I claim:
1. A device comprising:
 1) a first means for starting electrical stimulation of a first leg of a person when a distance between a reference point on the person's first leg and the surface on which the person walks exceeds a first predetermined value; and
 2) a second means for stopping electrical stimulation of the first leg of the person when the distance between the reference point on the person's first leg and the surface falls below a second predetermined value.

2. The device of claim 1 wherein the first predetermined value exceeds the second predetermined value.

3. The device of claim 1 wherein the first and second predetermined values are calculated on the basis of an initial recorded distance between the reference point on the person's first leg and the surface.

4. A functional electrical stimulator comprising:
1) a control unit removably attached to a first leg of a person standing on a surface, the control unit comprising a source of electrical power;
2) a first means of measuring in real time the distance between the control unit and the surface;
3) a second means for recording a reference distance between the control unit and the surface during an initialization procedure that occurs when the person is standing generally still with the first leg generally perpendicular to the surface;
4) a third means for continually comparing the real time distance measured to the reference distance, after the reference distance has been recorded; and
5) a fourth means for commanding an electrical signal to be generated and transmitted to a particular part of the first leg whenever the real time distance exceeds the reference distance by a first predetermined percentage, and continuing to generate and transmit the electrical signal until such time as the real time distance falls below a second predetermined percentage of the reference distance;
wherein the first predetermined percentage is greater than the second predetermined percentage.

5. The functional electrical stimulator of claim 4 further including:
1) a fifth means for ramping up the electrical signal from zero to full signal over a first predetermined period of time when the fourth means commands the electrical signal to be generated;
2) a sixth means for ramping down the electrical signal from full signal to zero over a second predetermined period of time when the fourth means ceases commanding the electrical signal;
wherein the second predetermined period of time is greater than the first period of time.

6. The functional electrical stimulator of claim 4 further including: a remote control means for controlling the control unit.

7. The functional electrical stimulator of claim 4 further including: a means for programming the control unit including means to program the first and second predetermined percentages.

8. The functional electrical stimulator of claim 4 wherein the control unit has a signal means for communicating multiple events to the person by generating and sending to the person's first leg a different pulse train for each one of the multiple events.

9. A method comprising the steps of:
1) measuring, in real time, the distance between a control unit removably attached to a first leg of a person and a surface on which the person stands;
2) recording a reference distance between the control unit and the surface at a time when the person is standing generally still and when the first leg is generally perpendicular to the surface;
3) thereafter, continually comparing the real time distance measured to the reference distance; and
4) generating an electrical signal and transmitting it to a part of the first leg of the person whenever the real time measured distance exceeds the reference distance by a first predetermined percentage, and thereafter continuing to generate and transmit the electrical signal until such time that the real time measured distance is less than a second predetermined percentage of the reference distance.

10. The method of claim 9 wherein the first predetermined percentage is greater than the second predetermined percentage.

11. The method of claim 9 wherein, during the electrical signal generation step, the electrical signal is ramped-up over a first predetermined period of time from zero to full signal.

12. The method of claim 9 wherein, when the real time measured distance is less than the second predetermined percentage of the reference distance, the electrical signal generated and transmitted to the first leg is ramped-down over a second predetermined period of time from full signal to zero.

13. The method of claim 9 wherein, during the electrical signal generation step, the electrical signal is ramped-up over a first predetermined period of time from zero to full signal; and wherein, when the real time measured distance is less than the second predetermined percentage of the reference distance, the electrical signal generated and transmitted to the first leg is ramped-down over a second predetermined period of time from full signal to zero; with the first predetermined period of time being shorter than the second predetermined period of time.

14. An electrical stimulation apparatus comprising:
1) a control unit removably attached to a person's first leg;
2) a means for initially measuring a reference distance between the control unit and the surface on which the person stands and walks, when the person is relatively stationary with the person's first leg relatively perpendicular to the surface;
3) a means for determining a first predetermined multiple of the reference distance, and for determining a second predetermined multiple of the reference distance;
4) a means for subsequently continuously measuring in real time the distance between the control unit and the surface, and for continuously comparing the real time measured distance with the reference distance; and
5) a means for generating and transmitting electrical stimulation to the first leg, the electrical stimulation ramping up to full value beginning when the real time distance exceeds the first predetermined multiple of the reference distance and ramping down from full value to zero beginning when the real time distance falls below the second predetermined multiple of the reference distance.

15. A means for providing electrical stimulation to a person comprising:
1) a source of electrical power;
2) a liner voltage regulator;
3) a programmable microcontroller powered by the source of electrical power; the microcontroller having an addressable analog-to-digital converter, a universal synchronous asynchronous receiver transmitter (USART), multiple input-output ports, and a nonvolatile memory;
4) at least one output circuit for delivering electrical stimulation to a person, each output circuit comprising:
  (a) a first switchable driver means for driving the primary winding of a first step-up transformer, and
  (b) a first means for applying power to a part of a person's body, the first means for applying power being connected across the secondary winding of the first step-up transformer;
5) a means for determining a first physical distance and producing an electrical signal that is proportional to the magnitude of the first physical distance; and 6) a means to receive programming information and transmit it to the programmable microcontroller;

wherein the microcontroller monitors the electrical signal that is proportional to the first physical distance, and commands each output circuit to deliver electrical stimulation to the person whenever the electrical signal equals a first predetermined level and, thereafter, continues commanding each output circuit to deliver electrical stimulation until the electrical signal reaches a second predetermined level, at which time the microcontroller ceases commanding each output circuit to deliver electrical stimulation until such time as the electrical signal equals the first predetermined level.

16. A means for providing functional electrical stimulation to a person comprising:
1) a source of electrical power;
2) a first diode having its anode connected to the positive terminal of the means for providing power;
3) a power switch having a first terminal connected to the cathode of the first diode and a second terminal connected to a first circuit bus line;
4) a liner voltage regulator having its input connected to the first circuit bus line, a first output connected to a second circuit bus line, and a second output connected to a third circuit bus line;
5) a capacitor having its positive terminal connected to the third circuit bus line and its negative terminal connected to the second circuit bus line;
6) a programmable microcontroller being powered by a connection to the third circuit bus line; the microcontroller having an addressable analog-to-digital converter, a universal synchronous asynchronous receiver transmitter, multiple input-output ports, and nonvolatile flash memory;
7) a distance means for determining a first physical distance wherein the distance means comprises a circuit that produces a first electrical signal that represents the first physical distance determined by the distance means;
8) means for transmitting the first electrical signal of the distance means to an input port of the microcontroller; and
9) at least one output circuit, each output circuit comprising:
   (a) a first NPN transistor having its collector connected to the first circuit bus line,
   (b) a first potentiometer having a first terminal connected to the emitter of the first NPN transistor,
   (c) a first resistor having a first terminal connected to a second terminal of the first potentiometer and having a second terminal connected to the second circuit bus line,
   (d) a first Darlington transistor having its emitter connected to the second circuit bus line, and its base connected to the adjustable terminal of the first potentiometer through a second resistor,
   (e) a first step-up transformer having one primary winding terminal connected to the collector of the first Darlington transistor and a second primary winding terminal connected to the first circuit bus line, and having its secondary winding connected across a first output power jack to which electrode pads may be connected,
   (f) a second diode connected in parallel to the primary winding of the first step-up transformer with the second diode's anode connected to the collector of the first Darlington transistor and the second diode's cathode connected to the first circuit bus line, and
   (g) a third resistor with a first terminal connected to the base of the first NPN transistor and a second terminal connected to an output port of the microcontroller.

17. The means for providing functional electrical stimulation of claim 16 wherein the distance means for determining a first physical distance is a distance measuring sensor which detects reflected infrared radiation.

18. The means for providing functional electrical stimulation of claim 16 further comprising a means for receiving a control signal from a remote control, a means for converting the control signal to an electrical signal, and a means for transmitting the electrical signal to an input of the microcontroller.

19. A means for providing functional electrical stimulation to a person comprising:
1) a source of electrical power;
2) a first diode having its anode connected to the positive terminal of the means for providing power;
3) a power switch having a first terminal connected to the cathode of the first diode and a second terminal connected to a first circuit bus line;
4) a liner voltage regulator having its input connected to the first circuit bus line, a first output connected to a second circuit bus line, and a second output connected to a third circuit bus line;
5) a capacitor having its positive terminal connected to the third circuit bus line and its negative terminal connected to the second circuit bus line;
6) a programmable microcontroller being powered by a connection to the third circuit bus line; the microcontroller having an addressable analog-to-digital converter, a universal synchronous asynchronous receiver transmitter, multiple input-output ports, and nonvolatile flash memory;
7) a distance means for determining a first physical distance wherein the distance means comprises a circuit that produces an first electrical signal that represents the first physical distance determined by the distance means;
8) means for transmitting the first electrical signal of the distance means to an input port of the microcontroller;
9) a first output circuit comprising:
   (a) a first NPN transistor having its collector connected to the first circuit bus line,
   (b) a first potentiometer having a first terminal connected to the emitter of the first NPN transistor,
   (c) a first resistor having a first terminal connected to a second terminal of the first potentiometer and having a second terminal connected to the second circuit bus line,
   (d) a first Darlington transistor having its emitter connected to the second circuit bus line, and its base connected to the adjustable terminal of the first potentiometer through a second resistor,
   (e) a first step-up transformer having one primary winding terminal connected to the collector of the first Darlington transistor and a second primary winding terminal connected to the first circuit bus line, and having its secondary winding connected across a first output power jack to which electrode pads may be connected,
   (f) a second diode connected in parallel to the primary winding of the first step-up transformer with the second diode's anode connected to the collector of the first Darlington transistor and the second diode's cathode connected to the first circuit bus line, and (g) a third resistor with a first terminal connected to the base of the first NPN transistor and a second terminal connected to an output port of the microcontroller; and 10) a second output circuit comprising:
   (a) a second NPN transistor having its collector connected to the first circuit bus line,
   (b) a second potentiometer having a first terminal connected to the emitter of the second NPN transistor,
   (c) a fourth resistor having a first terminal connected to a second terminal of the second potentiometer and having a second terminal connected to the second circuit bus line,
   (d) a second Darlington transistor having its emitter connected to the second circuit bus line, and its base connected to the adjustable terminal of the second potentiometer through a fifth resistor,
   (e) a second step-up transformer having one primary winding terminal connected to the collector of the second Darlington transistor and a second primary winding terminal connected to the first circuit bus line, and having its secondary winding connected across a second output power jack to which electrode pads may be connected,
   (f) a third diode connected in parallel to the primary winding of the second step-up transformer with the third diode's anode connected to the collector of the second Darlington transistor and the third diode's cathode connected to the first circuit bus line, and
   (g) a sixth resistor with a first terminal connected to the base of the second NPN transistor and a second terminal connected to an output port of the microcontroller.

20. The means for providing functional electrical stimulation of claim 19 wherein the distance means for determining a first physical distance is a distance measuring sensor which detects reflected infrared radiation.

21. The means for providing functional electrical stimulation of claim 19 further comprising a means for receiving an infrared signal from a remote control, a means for converting the infrared signal to an electrical signal, and a means for transmitting the electrical signal to an input of the microcontroller.

* * * * *